US005432395A

United States Patent [19]
Grahn

[11] Patent Number: 5,432,395
[45] Date of Patent: Jul. 11, 1995

[54] DIRECT-DRIVE FIELD ACTUATOR MOTORS

[75] Inventor: Allen R. Grahn, Salt Lake City, Utah

[73] Assignee: Bonneville Scientific Incorporated, Salt Lake City, Utah

[21] Appl. No.: 101,496

[22] Filed: Aug. 2, 1993

[51] Int. Cl.⁶ ............................................ H01H 41/08
[52] U.S. Cl. ............................... 310/328; 310/323
[58] Field of Search .............................. 310/323, 328

[56] References Cited

U.S. PATENT DOCUMENTS

| | | | |
|---|---|---|---|
| 2,439,499 | 4/1948 | Williams et al. | 310/328 |
| 3,835,338 | 9/1974 | Martin | 310/328 X |
| 3,902,084 | 8/1975 | May, Jr. | 310/328 |
| 3,952,215 | 4/1976 | Sakitani | 310/328 X |
| 4,195,243 | 3/1980 | Thaxter | 310/328 |
| 4,455,501 | 6/1984 | Tojo et al. | 310/328 |
| 4,578,607 | 3/1986 | Tojo et al. | 310/328 |
| 4,613,782 | 9/1986 | Mori et al. | 310/323 |
| 4,622,483 | 11/1986 | Staufenberg, Jr. et al. | 310/328 |
| 4,709,183 | 11/1987 | Lange | 310/328 |
| 4,743,792 | 5/1988 | Ueyama | 310/328 |
| 4,757,223 | 7/1988 | Veyama | 310/328 X |
| 4,775,815 | 10/1988 | Heinz | 310/328 |
| 4,782,262 | 11/1988 | Kiyo-Oka | 310/323 |
| 4,859,896 | 8/1989 | Anders, et al. | 310/328 X |
| 5,027,027 | 6/1991 | Orbach et al. | 310/328 X |
| 5,027,028 | 6/1991 | Skipper | 310/328 |
| 5,034,647 | 7/1991 | Ohtsuka | 310/328 |
| 5,039,894 | 8/1991 | Teter et al. | 310/328 X |
| 5,041,753 | 8/1991 | Clark et al. | 310/328 X |
| 5,079,471 | 1/1992 | Nygren, Jr. | 310/328 |
| 5,189,331 | 2/1993 | Mukohjima et al. | 310/328 |
| 5,204,577 | 4/1993 | Watanabe et al. | 310/328 |
| 5,216,313 | 6/1993 | Ohinishi et al. | 310/328 X |
| 5,216,314 | 6/1993 | Suzuki | 310/328 X |
| 5,245,232 | 9/1993 | Nihei et al. | 310/328 X |
| 5,252,870 | 10/1993 | Jacobsen et al. | 310/82 |
| 5,252,884 | 10/1993 | Dona | 310/328 |
| 5,254,898 | 10/1993 | Terajima | 310/321 |
| 5,264,755 | 11/1993 | Hettlage et al. | 310/328 |

FOREIGN PATENT DOCUMENTS

| | | | |
|---|---|---|---|
| 0157681 | 6/1988 | Japan | 310/328 |
| 0157682 | 6/1988 | Japan | 310/328 |
| 0174577 | 7/1988 | Japan | 310/328 |
| 0214272 | 8/1989 | Japan | 310/328 |
| 0308177 | 12/1989 | Japan | 310/328 |
| 0290170 | 11/1990 | Japan | 310/328 |
| 0858153 | 8/1981 | U.S.S.R. | 310/323 |

OTHER PUBLICATIONS

McCarty, Lyle, H., "Piezoelectric Actuators Generate Many Motion Patterns", *Design News*, 06/08/87, pp. 136–138.

Micro Pulse Systems, Inc. (brochure), "Linear Micropositioning with Micro Pulse Systems' Piezoelectric Actuators", undated.

Naik, Dipak, et al., "Magnetostricitive Direct Drive Motors", Technical Report ME & ES 92-2, University of North Carolina at Charlotte, Jun. 30, 1992, pp. 1–46.

PCIM Staff, "New Ideas in Motion", *PCIM*, Apr. 1987, pp. 37–40.

*Primary Examiner*—Mark O. Budd
*Attorney, Agent, or Firm*—Trask, Britt & Rossa

[57] ABSTRACT

A high-torque, low speed, positive-drive field actuator motor including a stator carrying at least one field actuator which changes in dimension responsive to application of an energy field, and at least one drive shoe movable by the dimensional changes of the field actuator to contact and move a rotor element with respect to the stator. Various embodiments of the motor are disclosed, and the rotor element may be moved linearly or arcuately.

31 Claims, 18 Drawing Sheets

|  | a | b | c | d | e | f | g | h |
|---|---|---|---|---|---|---|---|---|
| PZA 272 | E | 3/4 E | 1/2 E | 1/4 E | NE | 1/4 E | 1/2 E | 3/4 E |
| PZA 270 | 1/2 E | 3/4 E | E | 3/4 E | 1/2 E | 1/4 E | NE | 1/4 E |
| SHOE DIRECTION | D & R | D | U & R | U | U & L | U | D & L | D |
| ELEMENT DIRECTION | R | R | R | NM | NM | NM | NM | NM |

| | | | | | | |
|---|---|---|---|---|---|---|
| PZA 270 | NE | NE | E | NE | NE | E |
| PZA 272 | NE | E | E | NE | E | E |
| SHOE DIRECTION | NM | D | R | U & L | D | R |
| ELEMENT DIRECTION | NM | NM | R | NM | NM | R |
| | $t_0$ | $t_1$ | $t_2$ | $t_3$ | $t_4$ | $t_5$ | $t_6$ TIME → |

DIRECT-DRIVE FIELD ACTUATOR MOTORS

RIGHTS OF UNITED STATES GOVERNMENT

This invention was made with Government support under Contract No. DE-FG02-92ER81439 awarded by the Department of Energy. The Government has certain rights in the invention.

This invention was made with Government support under Contract Nos. NAS8-38914, NAS8-39362 and NAS7-1205 awarded by the National Aeronautics and Space Administration. The Government has certain rights in the invention.

BACKGROUND OF THE INVENTION

1. Field of the Invention

The present invention relates generally to motors, and more specifically to piezoelectric and other field actuator motors employing motive power elements which physically elongate, bend or otherwise change dimensions responsive to changes in electrical or magnetic fields.

2. State of the Art

Traditional electric motors cause a shaft or rotor to rotate by creating a magnetic field between a primary winding in a stationary portion, or stator, of the motor and a secondary winding associated with the shaft or rotor. Such motors are relatively large and heavy relative to output torque. Such motors, for many applications, must be connected to transmission systems that alter speed and torque output and, in some instances, convert the rotary movement of the motor rotor to linear movement. These transmission systems, however, add substantially to the size, weight and complexity of the motors. Altering the electrical power input to such motors also provides some adjustability of output, but in most instances such adjustability is limited in range and, as with transmission systems, adds bulk, complexity and cost to the motor system.

Various other types of electric motors have been developed that employ piezoelectric, magnetostrictive, or electrostrictive actuators as motive power elements, rather than magnetic attraction or repulsion as in traditional electric motors. A piezoelectric actuator has a first length when a first voltage (or electric field) is applied across it and a second length when a second voltage is applied across it. An electrostrictive actuator has a first length when a first voltage is applied across it and a second length when a second voltage is applied across it. A magnetostrictive actuator has a first length when a first magnetic field is applied to it and a second length when a second magnetic field is applied to it. As used herein, a term "field actuator" may refer to a piezoelectric, magnetostrictive, or electrostrictive actuator.

It is also contemplated that piezoelectric and other field actuators configured as "bending" actuators in structures which behave similar to bimetallic strips employed in thermostats are also encompassed by the term "field actuator," as are shape memory alloy structures exhibiting similar dimensional variances in response to temperature fluctuations. Therefore, it may also be suitable to characterize the term "field actuator" as encompassing structures adapted to vary in at least one dimension responsive to application or removal of any energy field.

Motors employing piezoelectric actuators as motive power elements have been used in the prior art to create linear and rotary movement. For example, U.S. Pat. No. 5,027,027 to Orbach et al. describes a linear motor referred to as an "Inchworm" motor that includes forward, center, and rear piezoelectrically activated cylindrical elements arranged about a shaft. The shaft is moved forward, for example, by clamping the forward element, extending the center element, clamping the rear element, and releasing the forward element.

U.S. Pat. No. 4,578,607 to Tojo et al. describes a system in which piezoelectric actuators move sections to rotate a disk. The disk is lowered onto the sections after which they are moved by the actuators. The disk is then raised while the actuators reset. Some actuators elongate during the time other actuators contract.

SUMMARY OF THE INVENTION

The present invention provides a unique, compact, high torque, variable speed motor adaptable to continuous or incremental movement, either linear or rotary, of a directly driven motor element.

The motor of the present invention is easily configured for a variety of applications, including fingers and thumbs of robotic hands, limb joints in a variety of robotic designs, electromechanical control systems and other uses where high torque or precision displacement control is desirable, as well as in traditional motor applications where small size, low weight and reliability are constraining design factors.

The motor of the present invention, as presently contemplated by the inventor and not by way of any limitation on other embodiments which may in the future fall within the ambit of the claims appended to this specification, is a stepper motor which may be structurally configured to perform as a "finger motor" a "star motor" or a "ratchet motor." All of the embodiments of the invention disclosed herein employ for motive power dimensional changes induced in field actuators (as previously defined herein) responsive to periodic fluctuations of electrical, magnetic or other energy fields, to drive linearly or rotationally movable elements, sometimes referred to herein as "rotors."

The finger motor, so called because of its ready applicability to use in digits of robotic or prosthetic hands, employs at least two mutually rotationally movable segments. A selectively energized first field actuator is employed as the motive power element for a clamping means for locking one segment to a rotatable driven element, and a selectively energized second field actuator is employed with the other segment as the motive power element for engaging the rotatable driven element when the first field actuator is energized to activate the clamping means. To provide more power and to effectuate substantially continuous movement by the rotated segment, two counter-rotating drive actuators may be employed, each periodically energized at the appropriate time in cooperation with a cooperating clamping actuator as will be hereinafter described.

The star motor, so called because of the resemblance of a rotary embodiment thereof in side or plan elevational view to a many-pointed star, employs as motive power elements one or more pairs of field actuators carried by a stator assembly to periodically drive a drive element or shoe against a resilient restraint in a rotational, ellipsoidal trajectory against a driven rotor element, which rotor element may in fact move rotationally or linearly, the term "rotor" being used only in the descriptive sense of identifying the element being moved with respect to the stator assembly. Depending upon the particular orientation desired, each of the field actuators of the pair may be oriented at an oblique angle to the surface of the rotor engaged by the drive shoe (hereinafter termed a "V-drive" motor), or one may be oriented substantially perpendicular to the rotor surface and one substantially parallel thereto (hereinafter termed an "L-drive" motor). Selective energizing and de-energizing of one or both actuators at appropriate times and for appropriate intervals, the exact sequence depending upon whether a V-drive or an L-drive is employed in the motor, results in the drive shoe engaging the rotor, translating in the direction of desired rotor movement and subsequently disengaging from the rotor and moving back to its starting position with respect to the actuators. Other actuator orientations and motor configurations are also disclosed.

The ratchet motor, so called due to the manner in which one or more drive field actuators act upon the rotor, is in some respects similar to the finger motor in that one or more field actuator-controlled clamping means are employed in combination with one or more drive actuators to transmit linear drive actuator movement to the rotor.

It should be understood and appreciated that the motor of the present invention may in many instances be fabricated by using existing parts of an assembly to be motorized. For example, in any rotating joint, there will normally be bearing means and a shaft interposed between structural members. By modifying the existing structure to accept actuators, and adding a few additional parts, a motor according to the present invention can be easily fabricated. The compactness of field actuators and their extremely high power density, in combination with the drive systems forming a part of the present invention, result in motors that can be very small and light relative to torque output, and which for the vast majority of preferred applications do not require a transmission.

DETAILED DESCRIPTION OF THE ILLUSTRATED EMBODIMENTS

As noted previously, the present invention contemplates at least three types of motor embodiments, which for convenience are referred to herein as a "finger motor," a "star motor," and a "ratchet motor." None of these motors requires a transmission for reducing a high rotor speed to enhance torque output, as in conventional electric motors, but instead may be termed a "direct drive" motor with respect to the digit, limb, valve or other structure to which the rotor is secured or engaged. The motor embodiments are hereafter discussed in detail in the above order of reference.

A. Finger Motor

The finger motor received its name because its applications include use in robotic or artificial human (prosthetic) fingers. The finger motor uses one or more oscillating drive structures and one or more oscillating clamping structures to cause one segment on the finger motor to rotate with respect to another segment, similar to the way one segment of a human finger rotates with respect to another segment about a knuckle joint. The term "oscillating" as used herein denotes a structure including an element which may be selectively caused, responsive to application of an appropriate electrical, magnetic or other energy field, to change in at least one dimension such as length or width, or to change in shape (for example, to bend), and to return to its original dimension or shape responsive to the removal of the field or to application of a field of opposite polarity. Such changes, induced on a periodic basis, are employed to drive the motors of the present invention.

Described in terms analogous to electrical terminology, the finger motors of the present invention may be described as mechanical rectifiers which employ a single direction of the back-and-forth motion of expanding and contracting field actuators to develop large linear or rotational motion of a driven motor element.

1. A First Preferred Embodiment

FIGS. 1-6 illustrate a first preferred embodiment of a finger motor according to the present invention.

Figure 1:
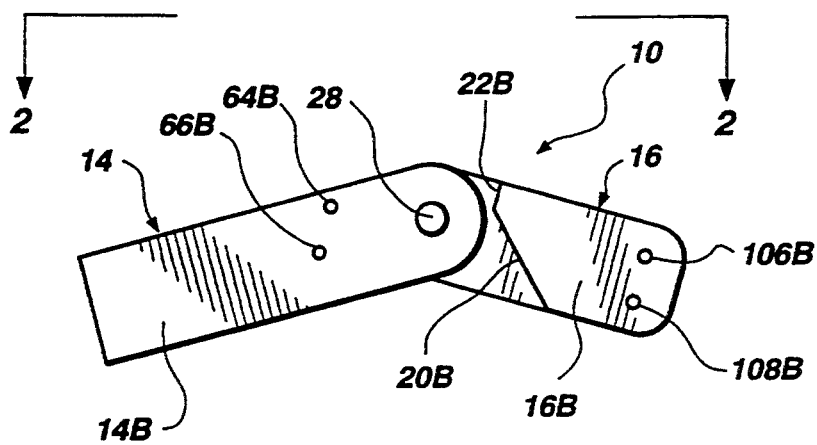
FIG. 1 is a side elevation of a finger motor assembly according to a first preferred embodiment of the present invention.

FIG. 1 shows a side view of a finger motor assembly 10, including a first segment 14 and a second segment 16, which is rotatably secured to segment 14 and, as disclosed, rotates with respect to segment 14 as motor 10 operates. (It is assumed that segment 14 is held stationary so that segment 16 rotates. Alternatively, segment 16 could be held stationary, so that segment 14 would rotate.) Segment 14 includes two oscillating drive structures and segment 16 includes two oscillating clamping structures.

Segment 16 includes a ridge 20B that ultimately limits clockwise movement of segment 16 (as viewed in FIG. 1) with respect to segment 14 and a ridge 22B that limits counterclockwise movement of segment 16 with respect to segment 14. The shapes and positions of ridges 20B and 22B may be changed as desired to allow different limitations on the range of clockwise and counterclockwise movement of segment 16 relative to segment 14.

Figure 2A:
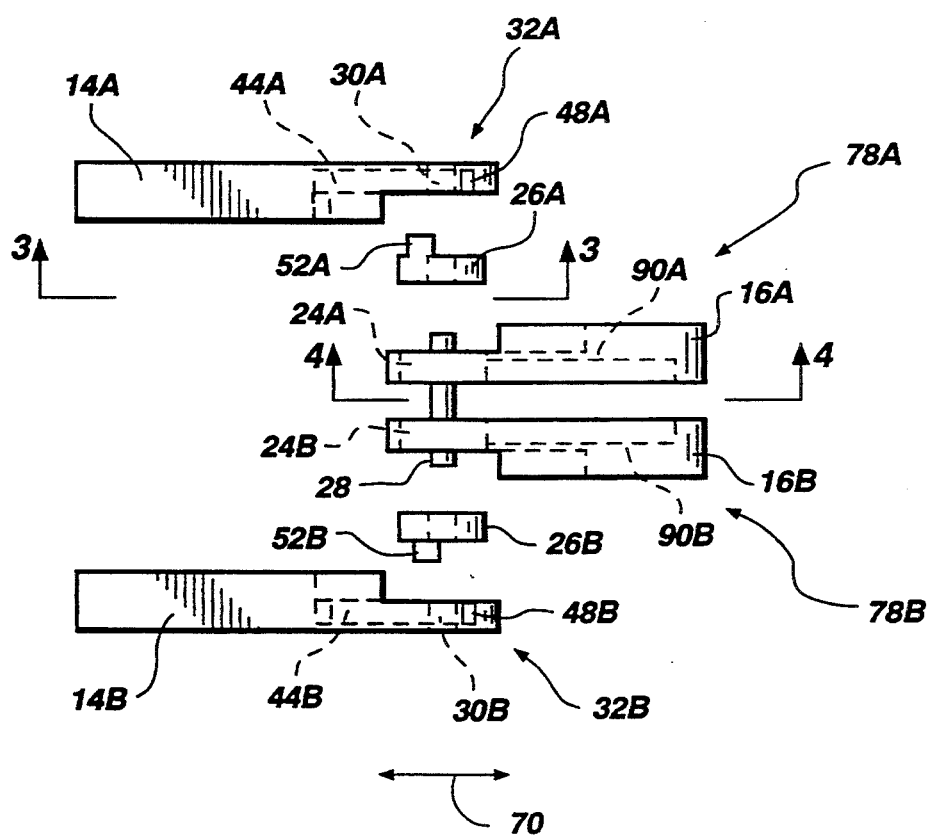
FIG. 2A is an exploded top elevation of the finger motor assembly of FIG. 1 as viewed from line 2—2 of FIG. 1.
Figure 2B:
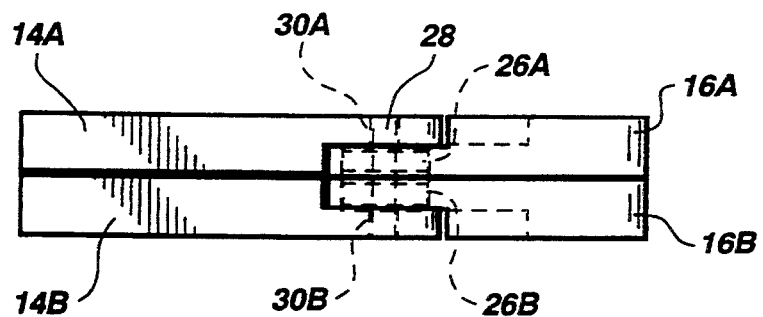
FIG. 2B is a top elevation of the finger motor assembly as viewed from line 2—2 of FIG. 1.
Figure 2C:
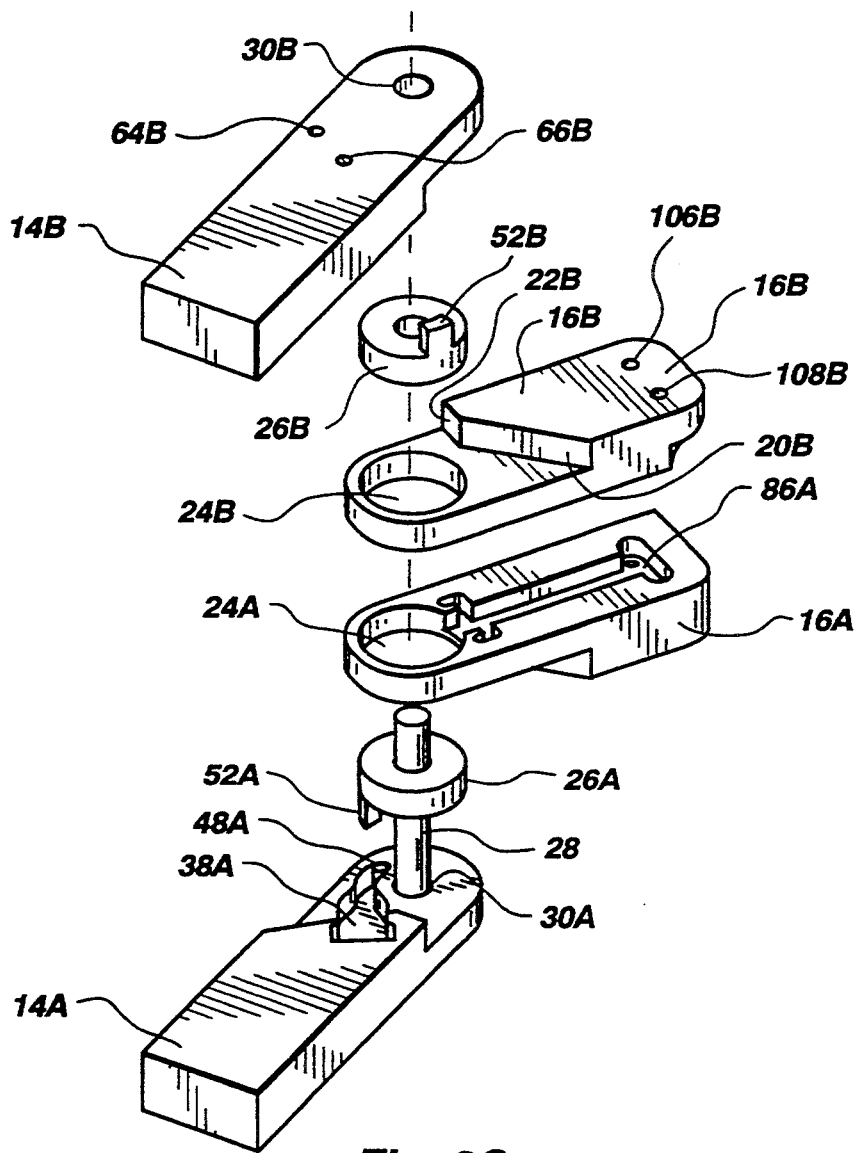
FIG. 2C is a perspective view of a portion of the finger motor assembly of FIG. 2B.

FIG. 2A shows an exploded top view of finger motor assembly 10 as viewed from line 2—2 of FIG. 1. FIG. 2B shows a top view of finger motor assembly 10 as viewed from line 2—2 of FIG. 1. For convenience in construction and assembly of finger motor 10, segment 14 may be comprised of subsegments 14A and 14B, which are manufactured separately and joined together at final assembly. Likewise, segment 16 may be comprised of subsegments 16A and 16B, which are manufactured separately and joined together at final assembly. The subsegments may be joined together to form a segment by pins, screws, brackets, adhesive, or other conventional means known in the art. Subsegment 14A is the mirror image of subsegment 14B. Subsegment 16A is the mirror image of subsegment 16B, except as noted hereafter with respect to the orientation of the oscillating drive structure carried thereby in a modification of the preferred embodiment. In this description and in the drawing figures, a reference number followed by the letter "B" identifies a component which is the same as or generally a mirror image of a component identified with the same reference number followed by the letter "A." For example, subsegment 16A includes exterior ridges 20A and 22A (not shown), which are the mirror images of ridges 20B and 22B.

Subsegments 16A and 16B include aligned bushing cavities 24A and 24B, which cavities have diameters that are slightly larger than the diameter of rotary drive elements comprising bushings 26A and 26B. A cylindrical rod, such as knuckle pin 28, extends through bushings 26A and 26B retained in bushing cavities 24A and 24B, and is secured at each end by means known in the art in pin receptacles 30A and 30B in segments 14A and 14B, respectively. Bushings 26A and 26B freely rotate within bushing cavities 24A and 24B, and about knuckle pin 28. A shim or spacer (not shown) may separate segments 14A and 14B when assembled as segment 14 of finger motor 10, in order to provide appropriate clearance for movement of segment 16 with respect thereto.

Figure 3:
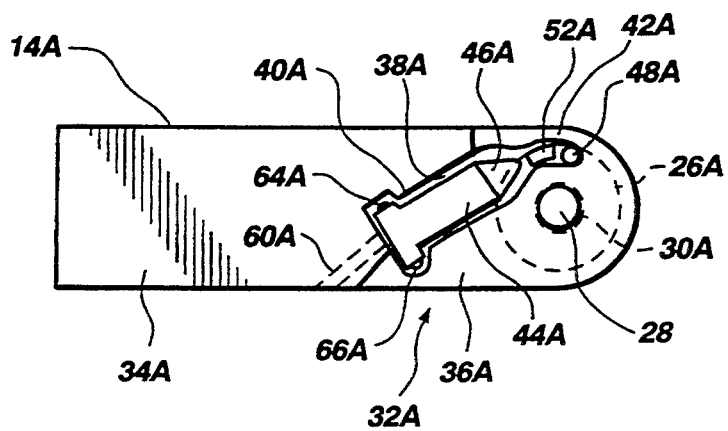
FIG. 3 is a side view of a drive subsegment of the finger motor assembly as viewed from line 3—3 of FIG. 2A.

Oscillating drive structures 32A and 32B are described in connection with FIG. 3, which shows a side view of subsegment 14A viewed from line 3—3 of FIG. 2A. Referring to FIG. 3, subsegment 14A includes parallel but laterally offset surfaces 34A and 36A, as well as a slot 38A, which is formed in surface 36A. Slot 38A includes a major portion 40A shaped to hold a piezoelectric or other field actuator (hereinafter referred to generically as a "PZA") 44A of similar configuration, and an arcuate minor portion 42A into which extends drive shoe 46A adjacent to PZA 44A. Minor slot portion 42A also receives at its distal end an elastic or otherwise resilient return member 48A, and drive pin 52A which extends laterally from bushing 26A (lines) at the periphery thereof (see FIG. 2A) into minor slot portion 42A between drive shoe 46A and return member 48A. In this first embodiment, oscillating drive structure 32A includes PZA 44A, drive shoe 46A and return member 48A. Completing the description of subsegment 14A, a threaded hole 60A aligned with the longitudinal axis of PZA 44A receives a screw (unnumbered) used to adjust the position of PZA 44A in major slot portion 40A so that expansion of PZA 44A will result in movement of drive shoe 46A against drive pin 52A. A shim may be placed between the screw and PZA 44A. Holes 64A and 66A receive wires from a control circuit 74, shown in FIG. 5, to apply a control signal to drive PZA 44A.

The control or drive signal applied to PZA 44A may be selected from a variety of waveforms such as, by way of example and not limitation, a sinusoidal wave, a triangular wave, a square wave, or a rectangular-shaped wave. When the voltage of the control signal increases from a voltage V1 (which may be zero volts or "ground" or even a negative voltage) to a voltage V2, the length of PZA 44A increases so as to move drive shoe 46A against drive pin 52A in the clockwise direction against elastic return member 48A, compressing the latter. Of course, bushing 26A rotates with movement of drive pin 52A, and when segment 16 is clamped to bushing 26A as hereinafter described, segment 16 will rotate with bushing 26A. When the voltage of the control signal decreases from voltage V2 to voltage V1, the length of PZA 44A decreases and the stored energy in compressed return member 48A moves drive pin 52A in the counter-clockwise direction. The parameters of PZA 44A and its driving waveform, and elastic member 48A are chosen so bushing 26A rotates between clockwise and counter-clockwise directions.

Oscillating drive structure 32B includes PZA 44B, drive shoe 46B and return member 48B, these and the other elements comprising segment 14B being substantially identical in material and configuration to those corresponding elements previously described with respect to segment 14A. Use of a second oscillating drive structure 32B thus provides for continuous driving of segment 16 as, while drive structure 32A is being "reset" by contraction of PZA 44A and movement of bushing 26A by return member 48A, drive structure 32B is driving segment 16 via bushing 26B in a ratchet-like phenomenon. It will be appreciated that distal segment 16 may be counter-rotated back to its initial position by using the force of elastic return members 48A and 48B and re-timing the clamping structures 78A and 78B accordingly, as hereinafter described. Alternatively, the clamping structures may merely be de-energized, and segment 16 may then swing freely about knuckle pin 28 with respect to segment 14. This feature is contemplated as having utility if it is desired to withdraw a robotic hand from an obstructed passage. The driving waveform for PZA 44B would normally be substantially identical to that for PZA 44A.

Another alternative for positive counter-rotation is to reorient slot 38B in segment 14B to drive bushing 26B in a counterclockwise direction responsive to elongation of PZA 44B. With reference to FIG. 3 of the drawings, the orientation of slot 38B in the direction of drive in such modification would be described as downward and to the right, in contrast to the drive direction of slot 38A, which would be described as upward and to the right. Thus, bushing 26B will, like bushing 26A, be caused to rotate between counter-clockwise and clockwise directions. However, unlike bushing 26A, movement of bushing 26B in the counter-clockwise direction will be caused by an increase in the length of PZA 44B and movement in the clockwise direction will be caused by the stored energy of compressed elastic return member 48B.

Figure 4:
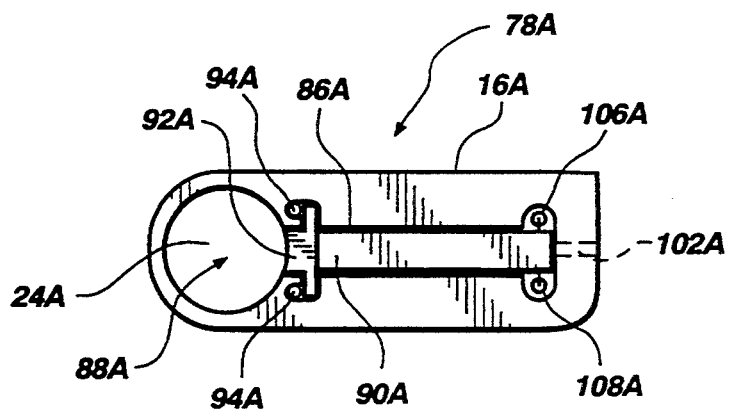
FIG. 4 is a side view of a clamp subsegment of the finger motor assembly as viewed from line 4—4 of FIG. 2A.

Oscillating clamping structures 78A and 78B are described in connection with FIGS. 2A and 2B, and FIG. 4, which shows a side view of subsegment 16A viewed from line 4—4 of FIG. 2A. Referring to FIG. 4, subsegment 16A includes previously referenced bushing cavity 24A, which has a diameter that is slightly larger than the diameter of bushing 26A. Subsegment 16A also includes a slot 86A, which is preferably oriented in alignment with a radial line from the center 88A of bushing cavity 24A and shaped to hold a PZA 90A and a clamping shoe 92A adjacent to PZA 90A. In this first embodiment, clamping structure 78A includes PZA 90A and clamping shoe 92A. Clamping structure 78B includes PZA 90B and clamping shoe 92B.

A threaded hole 102A receives a screw used to adjust the position of PZA 90A. A shim may be placed between the screw and PZA 90A. Holes 106A and 108A receive wires from control circuit 74 to apply a control signal to drive PZA 90A.

As with PZA 44A the control or drive signal applied to PZA 90A may be selected from a variety of exemplary waveforms such as a sinusoidal wave, a triangular wave, a square wave, or a rectangular-shaped wave, but in practice no particular waveform is required, since clamping PZA 90A is either "on" or "off."

However, if a square wave is employed as the control or drive signal PZA 90A, it is preferred that a resistance be placed in series with the actuator to slow down the speed of the wave form during the energizing portion of the cycle, to reduce impact forces between components, with attendant wear and noise reduction.

When the voltage of the control signal increases from a voltage V3 (which may be zero volts or even a negative voltage) to a voltage V4, the length of PZA 90A increases so as to move clamping shoe 92A against bushing 26A with sufficient force so that subsegment 16A locks with bushing 26A (i.e., subsegment rotates if bushing 26A rotates and does not rotate if bushing 26A does not rotate). Voltages V3 and V4 may, in fact, correspond to V1 and V2. When the voltage of the control signal decreases from voltage V4 to voltage V3, the length of PZA 90A decreases so that shoe 92A does not press against bushing 26A with significant force and segment 16A does not rotate with bushing 26A. As with oscillating drive structures 32, one or more elastic return members 94A may easily be incorporated into clamping structure 78 to positively bias clamping shoe 92A against PZA 90A and to reduce the force applied by clamping shoe 92A against bushing 26A when PZA 90A is in its contracted state.

As previously noted, segment 16B is a mirror-image twin of segment 16A, and the oscillating clamping structure 78A is substantially identical to structure 78B. As with PZA 90A, the control signal applied to PZA 90B controls whether clamping shoe 92B does or does not press against bushing 26B with a force sufficient to cause segment 16B to lock with bushing 26B.

Figure 5:
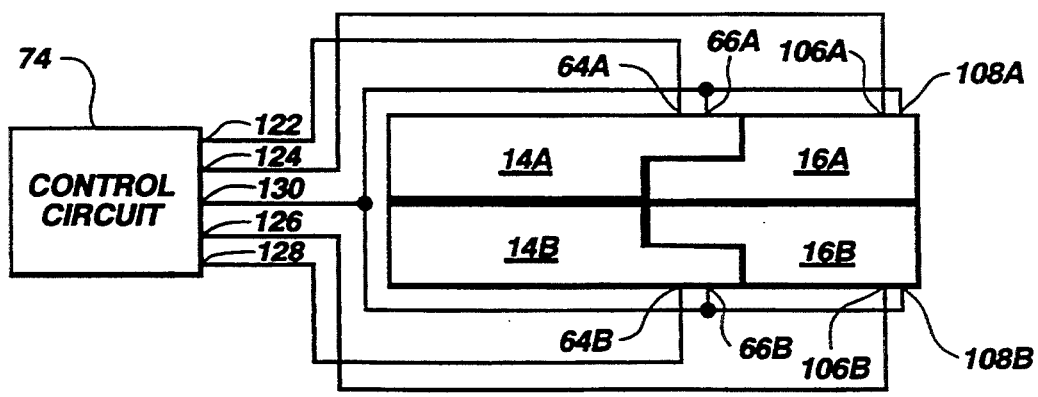
FIG. 5 is a partial schematic view of a control circuit and interconnections to piezoelectric actuators employed in the finger motor assembly of FIG. 1.

Referring to FIG. 5, control circuit 74 (which may be characterized as an energy source to drive the field actuators) is connected to PZA's 44A, 44B, 90A, and 90B through conductors such as wires, which are preferably secured to the sides of segments 14 and 16. Control circuit 74, which may be generally termed the piezoelectric motor drive electronics, is designed to produce phased voltage waveforms such as the square waveforms depicted in FIG. 6. Applied voltage may commonly range from −40 V to +500 V, depending upon the particular actuator selected. Digital logic circuitry is employed to generate logic-level pulses, the timing of which can be easily adjusted, as the circuitry employs shift registers and counters driven by a system clock, all as known in the art. The clock is preferably a function generator so that clock frequency fluctuations may be employed to alter motor speed proportionally. Low voltage logic-level pulses drive the gates of MOSFETS, which in turn apply the control signals to the actuators. A resistor is employed in series with the actuator leads to decouple the capacitive load of the actuators and to limit the current during both energizing and de-energizing of the actuators.

All of the aforementioned components being commercially available and assembly thereof into a workable control circuit 74 being well within the ability of one of ordinary skill in the art, no further description of control circuit 74 except as to its function will be made. It should be understood that control circuit 74 does not form a part of the present invention, except insofar as it provides suitably shaped and timed signals to energize and de-energize the PZA's. Control circuit 74 may respond to real-time control by external control devices, for example directly tracking the movement of a human operator's fingers, or may be pre-programmed to operate in a variety of sequences. In either instance, such control methodology is known in the art and forms no part of the present invention. It will be appreciated and understood by those of ordinary skill in the art that field actuators other than the piezoelectric type may require a modified control circuit or energy source, but such modification is easily effected and is within the ability of those skilled in the art.

Control circuit 74 includes outputs 122, 124, 126, 128, and 130. Output 130 provides a ground potential. The control signal applied to PZA 44A is delivered to outputs 122 and 130, which are connected to PZA 44A by conductors passing through holes 64A and 66A. The control signal applied to PZA 90A is delivered to outputs 124 and 130, which are connected to PZA 44A by electrical conductors (such as wires) passing through holes 106A and 108A. The control signal applied to PZA 44B is delivered to outputs 128 and 130, which are connected to PZA 44B by conductors passing through holes 64B and 66B. The control signal applied to PZA 90B is delivered to outputs 126 and 130, which are connected to PZA 90B by conductors passing through holes 106B and 108B.

The rotation of segments 16A and 16B with respect to segments 14A and 14B, and thus the operation of finger motor assembly 10, is induced and controlled as follows. When it is desired that segments 16A and 16B rotate in the clockwise direction, PZA 90A is energized during the time bushing 26A is to be caused to rotate in the clockwise direction by the expansion of PZA 44A, and PZA 90B is then energized in conjunction with PZA 44B to rotate bushing 26B while bushing 26A is released from segment 16 and rotates counterclockwise. It is noted that bushing 26A turns through a very small arc, for example 0.15°–0.3°, during each expansion of PZA 44A, although the expansion of PZA 44A in a human-finger sized motor provides a relatively large force, typically 21 kg. Therefore, finger motor 10 may be described as a high-torque, low-speed motor. When it is desired that segments 16A and 16B rotate in the counterclockwise direction, PZA 90B is energized during the time bushing 26B is to be caused to rotate in the counter-clockwise direction by expansion of PZA 44B, and PZA 90A is not energized, except as described below.

Figure 6:
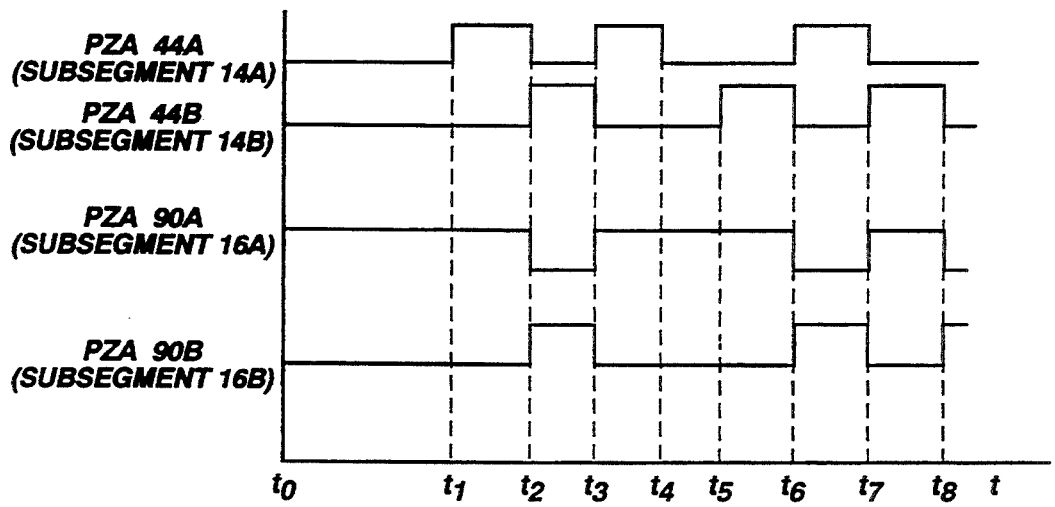
FIG. 6 is a graphic representation of a preferred sequence of energized and de-energized states of the actuators employed in the finger motor assembly of FIG. 1.

FIG. 6 graphically illustrates a preferred sequence of energized and de-energized states of PZA's 44A, 44B, 90A, and 90B using square wave control signals for controlling the position of segment 16. In FIG. 6, the x-axis represents time and the y-axis represents whether PZA's 44A, 44B, 90A, and 90B are in the energized or de-energized state, the de-energized states being represented by the corresponding wave form baselines, and the fully energized states by the tops of the square waves.

From time t0 to time t1, control circuit 74 determines that segment 16 should not rotate. Therefore, from time t0 to time t1, the state of PZA's 44A and 44B remains constant. To prevent gravity from pulling segment 16 rotationally downward about knuckle pin 28, at least one of PZA's 90A and 90B (e.g., PZA 90A) should be energized to lock a bushing to segment 16, rotation thereby being prevented by the limited travel of the bushing's drive pin. It should be noted that more than adequate locking torque to prevent rotation of segment 16 is available from PZA 90A, and that if more is required a larger PZA may be employed, or both PZA 90A and 90B may be energized.

Shortly before time t1, control circuit 74 determines that segment 16 should rotate in the clockwise direction from time t1 to time t4. Accordingly, from time t1 to time t4, PZA 44A alternates between energized and de-energized states, as does PZA 44B, which is energized during alternate periods to those in which PZA 44A is energized PZA 90A should be energized and PZA 90B should be de-energized during the time PZA 44A is energized and causes drive shoe 46A to move drive pin 52A and thus cause bushing 26A to turn clockwise. PZA 44A remains energized until time t2, which corresponds to the time at which bushing 26A stops rotating clockwise and elastic return member 48A is fully compressed. To prevent gravity from pulling segment 16 rotationally downward, there should be no time or essentially no time during which PZA 90A and PZA 90B are both de-energized. At about time t2, there is a short period of time during which bushing 26A has essentially no clockwise or counter-clockwise movement. PZA 90B is energized and PZA 90A is de-energized during this short period of time. It is preferred under some circumstances that PZA 90B be energized before PZA 90A is de-energized so as to prevent segment 16 from rotating counterclockwise responsive to the expansion of elastic return member 48A when PZA 44A is de-energized.

However, this requirement is dependant upon several factors. For example, at lower frequencies (such as 500 Hz or less) of energization pulses or waves for PZA 44, there may be a greater tendency or opportunity for segment 16 to rotate counter to the intended direction of movement due to gravity or other loads, as well as to return forces of elastic return member 48A when PZA 44A is de-energized. However, the reversal of movement direction of segment 16 responsive to expansion of return member 48A can be minimized by appropriate early timing of the de-energization of PZA 90A and release of clamping shoe 92A as PZA 44A nears the extent of its expansion. Operation of finger motor 10 at higher frequencies (for example, above 1 kHz) reduces slippage due to loading on segment 16 as the drive strokes of drive shoe 46A occur in such rapid succession, so that energization of PZA 90B prior to de-energizing PZA 90A may be necessary only under high load conditions.

From about time t2 to about time t3, bushing 26A freely rotates in the counter-clockwise direction under the return force of elastic member 48A. However, PZA 90B is energized as is PZA 44B, so bushing 26B, and segment 16, again rotate in the clockwise direction to the limit of travel of drive pin 52B, at which time, about t3, PZA 44B is de-energized. At about time t3, there is a short period of time during which both bushings 26A and 26B have essentially no clockwise or counter-clockwise movement. PZA 90A is energized and PZA 90B is de-energized during this short period of time. Again, as noted above, PZA 90A may or may not be energized before PZA 90B is de-energized, to prevent slippage of segment 16 with respect to segment 14.

At about time t3 and subsequent to energization of PZA 90A, PZA 44A is energized causing bushing 26A to again rotate clockwise. PZA 44A remains energized until time t4, which corresponds to the time at which bushing 26A stops rotating clockwise because elastic member 48A is fully compressed. During the same period, bushing 26B freely rotates counter-clockwise since PZA 90B has been de-energized. At about time t4, there is a short period of time during which bushings 26A and 26B have essentially no clockwise or counter-clockwise movement. PZA 90B would again be energized and PZA 90A de-energized during this short period of time in preparation for energization of PZA 44B to drive bushing 26B.

However, at time t4, control circuit 74 determines that segment 16 should rotate counter-clockwise from time t5 to time t8 and determines that PZA 90A should remain energized to lock segment 16 in place. Then, from time t5 to time t8, again PZA 44B alternates between energized and de-energized states with PZA 44A. However, to achieve counter-clockwise rotation of segment 16, PZA 90B and PZA 90A should each be energized during the time its associated bushing 26A or 26B is turned counter-clockwise responsive to the return force of the stored energy in a return member 48A or 48B. PZA 44B remains energized from time t5 to time t6, which corresponds to the time at which bushing 26B (and segment 16) stops rotating counter-clockwise because elastic member 48B is fully compressed. At about time t6, there is a short period of time during which bushing 26B has essentially no clockwise or counter-clockwise movement. PZA 90B is then energized and PZA 90A is de-energized during this short period of time, and bushing 26B and segment 16 are rotated in a counter-clockwise direction by return member 48B from about time t6 to about time t7. Also during time t6 to t7, PZA 44A is energized to load return member 48A. At about time t7, there is a short period of time during which bushing 26B has essentially no clockwise or counter-clockwise movement. PZA 90A is then energized and PZA 90B is de-energized during this short period of time, and bushing 26A and segment 16 rotated in a counter-clockwise direction.

At about time t7, PZA 44B is energized, causing bushing 26B to rotate counter-clockwise. PZA 44B remains energized until time t8, which corresponds to the time at which bushing 26B (and segment 16) stops rotating clockwise because elastic member 48B is fully compressed. At about time t8, there is a short period of time during which bushing 26B has essentially no clockwise or counter-clockwise movement. PZA 90B is energized and PZA 90A is de-energized during this short period of time, and bushing 26B and segment 16 are rotated counter-clockwise.

The piezoelectric actuators which comprise the motive power elements in the preferred embodiments of the invention are polycrystalline ceramic materials such as barium titanate and lead zirconate titanate. Such piezoelectric ceramics must be poled for the piezoelectric phenomenon to occur, and such process being well known in the art it will not be described herein.

In order to form an actuator, it is common to stack a large member of individual ceramic wafer elements in series and to then wire the elements in parallel. The longer or higher the stack, the greater the displacement of the actuator when it is energized. Piezoelectric actuators are now commercially available to produce strains of almost 0.1% at voltages as low as 100 V, and greater strains at higher voltages have been observed. Such actuators possess individual layers of about 0.1 mm thickness, the layers consolidated by a high pressure solid sintering process.

Characteristics of two suitable piezoelectric actuators of different size and dimensions are set forth below:

| Size | 2 mm × 3 mm × 9 mm | 2 mm × 3 mm × 18 mm |
| --- | --- | --- |
| Max. Voltage | 100 V | 100 V |
| Displacement | 6.5 microns/100 v. | 15 microns/100 v |
| Generated Force | 21 kg | 21 kg |
| Self Resonant Freq. | 150 kHz | 75 kHz |
| Static Capacitance | 175 nF | 400 nF |
| Dissipation Factor | 3.5% | 3.5% |
| Number of Layers | 64 | 144 |
| Compressive Strength | 9000 kg/cm2 | 9000 kg/cm2 |
| Tensile Strength | 50 kg/cm2 | 50 kg/cm2 |
| Mass | 0.5 g | 0.9 g |

The smaller actuators are suitable for use as drive PZA's, while the larger ones have been found useful as clamping PZA's, in human-sized robotic fingers.

Piezoelectric actuators suitable for use in finger motor 10 as well as in other embodiments of the invention are commercially available, by way of example and not limitation, from NEC, Tokyo, Japan; Tokin Corporation, Tokyo, Japan; Sensor Technology Limited, Collingwood, Ontario, Canada; and Dr. Lutz Pickelmann, Piezomechanik Optik, Munich, Federal Republic of Germany. Such actuators, as with substantially all PZA's, develop maximum force at zero displacement and zero force at maximum displacement.

Such actuators at temperatures below about 150° C. have a high resistance, on the order of $10^{11}$ ohms. Thus, under static operating conditions (after expansion) virtually no current is drawn nor power consumed in maintaining a state of activation. In other words, if it is desired to immobilize the digits of a robotic or prosthetic hand in a particular position, the power draw is negligible, a major advantage when using portable or otherwise limited electrical power sources.

It was also discovered that applications of voltages to certain PZA's suitable for use in the present invention from a negative range (rather than for zero volts or ground) increased the actuator elongation or displacement achieved, and suitable circuitry may be employed to take advantage of this known phenomenon if desired.

It is notable that, in an application such as powering digits or "fingers" of human-sized robotic hands, the additional mass of incorporating piezoelectric motors according to the present invention into the fingers may be less than 10 grams per joint or segment, inclusive of all necessary components as described above. Of course, larger actuators are available and might be incorporated in scaled-up, much larger hands for handling heavy objects.

Materials for the finger motor according to the present invention may be selected according to the contemplated operating environment, but ideally should be, in general, light and strong. For example, segments 14 and 16 may be of high strength aluminum, and bushing 26 and knuckle pin 28 of steel or stainless steel. More exotic segment materials include titanium, and bushings may be machined from a variety of alloys as known in the art, such as brass, beryllium copper or Inconel ® metal.

Elastic return members 48A may be coil springs, elastomeric stops or plugs, leaf or torsion springs, Belleville washers, or other means known in the art.

2. Alternative Preferred Embodiments

As previously noted, the invention may employ field actuators other than PZA's, such as magnetostrictive or electrostrictive actuators.

Figure 7:
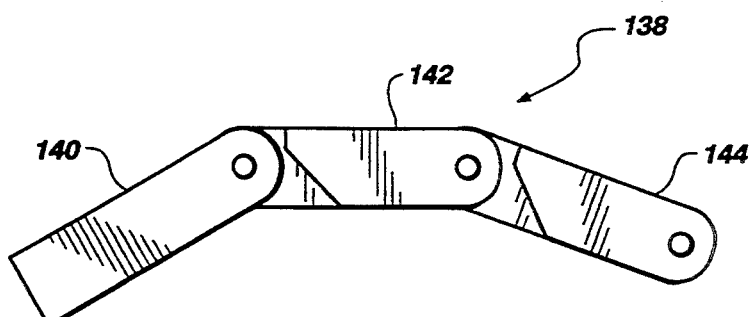
FIG. 7 schematically illustrates a three-segment finger motor according to the present invention.
Figure 8:
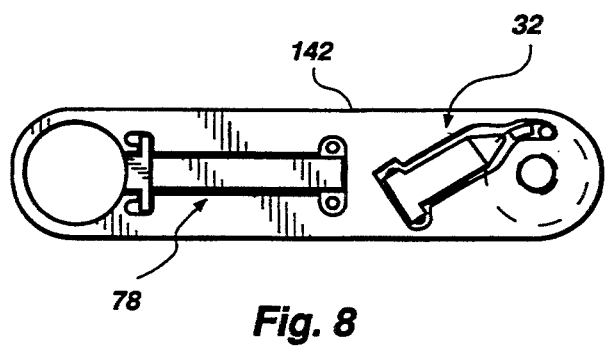
FIG. 8 shows a segment having both a drive structure and a clamping structure, suitable for employment in at least the middle segment of the three-segment finger motor of FIG. 7.

The finger motor may have more than two segments. For example, FIG. 7 shows a three-segment mechanical finger motor 138 having segments 140, 142, and 144. Basal segment 140 may be held stationary allowing proximal segment 142 and distal segment 144 to rotate. Proximal segment 142 may include both oscillating drive structures 32 and clamping structures 78, as schematically shown, for example, in FIG. 8, so as to have the ability to move responsive to an oscillating drive structure in basal segment 140, and to move distal segment 144 having a clamping structure.

Figure 9:
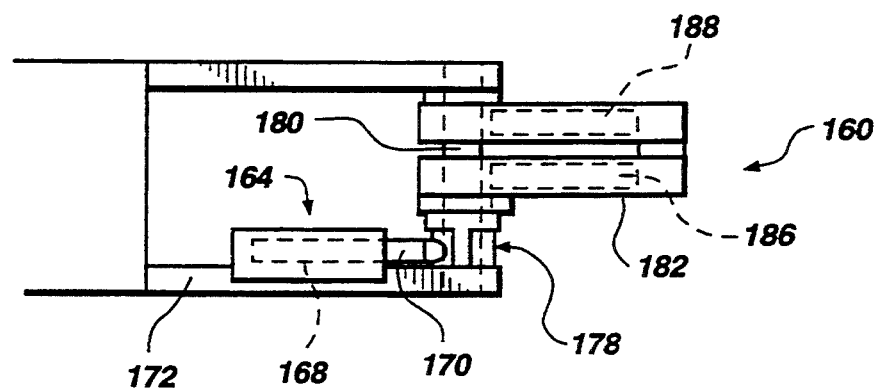
FIG. 9 is a top view of an alternative embodiment of a finger motor according to the present invention.
Figure 10:
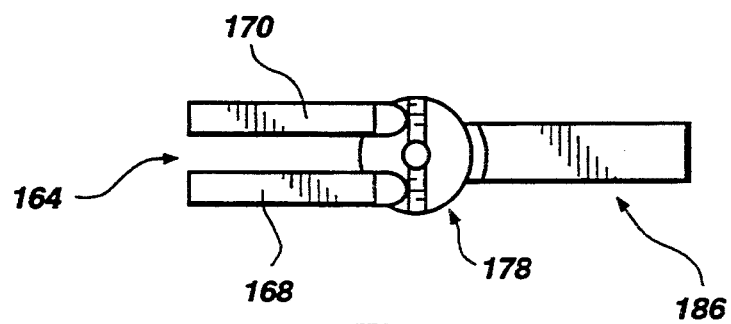
FIG. 10 is a side or plan view of the finger motor drive structure of FIG. 9.

FIGS. 9 and 10 show an alternative embodiment of finger motor 10 employing a positive, rather than resilient or elastic, return for the rotator bushing. A finger motor 160 includes an oscillating drive structure 164, which includes two PZA's 168 and 170 and is supported by a support 172. PZA's 168 and 170 alternately expand to push against a rotator 178 rotationally mounted on a fixed shaft 180 to which distal segment 182 is attached. Two oscillating clamping structures 186 and 188 are employed. Activation of structures 186 and 188 are timed so that the rotor 178 moves distal segment 182 in a clockwise direction by activation of PZA 170 and clamping of rotator 178 by clamping structure 186, distal segment 182 being subsequently locked in place on shaft 180 by clamping structure 188 when rotator 178 is being returned to its start position by PZA 168. When rotation direction is to be reversed, PZA 168 becomes the power PZA, and PZA 170 the return.

Figure 10A:
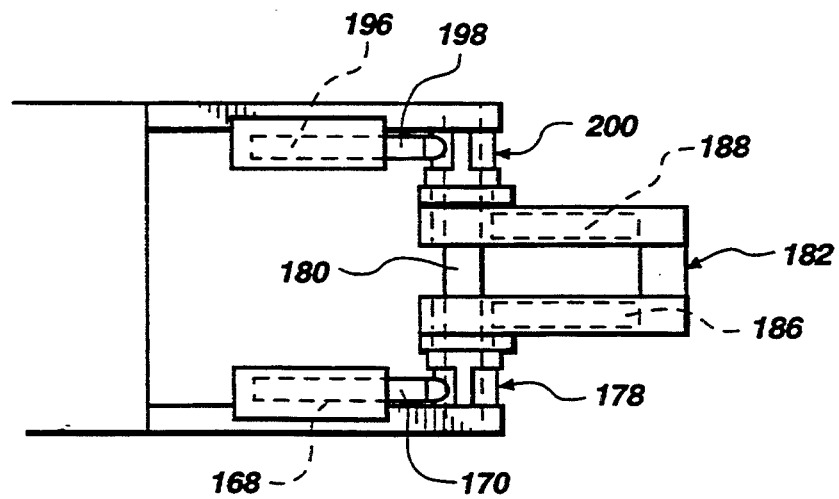
FIG. 10A is a top view of a modification of the alternative embodiment of the finger motor of FIGS. 9 and 10.

The embodiment of FIGS. 9 and 10 may be further modified by employing a second set of drive PZA's 196 and 198 to drive a second rotator 200, as shown in FIG. 10A. By employing such an arrangement, distal segment 182 could be continuously driven, as rotator 178 could drive segment 182 while rotator 200 is being reset to its start position, thus substantially doubling potential rotation speed while maintaining applicable torque.

In the example illustrated in connection with FIG. 6, prior to time t1, PZA 90A was already in the elongated state and PZA 90B was in the shortened state. Under a first computer program (followed in the FIG. 6 example), PZA 90B would remain in the shortened state unless it was necessary for it to be elongated. Under a second computer program, both PZA 90A and PZA 90B would be elongated prior to the beginning of a rotation sequence.

In the first preferred embodiment, in response to being energized, the PZA's are elongated and shortened in the direction of arrows 70 in FIG. 2A. However, as previously noted, bending type field actuators are known and may be suitable for some applications of the present invention where greater displacements (and thus motor speed) are desirable, and force (and thus motor torque) is less critical.

The first preferred embodiment could be modified if desired so that section 14 includes one oscillating drive structure and one clamping structure and section 16 could include one oscillating drive structure and one clamping structure, instead of the arrangement of the preferred embodiment, where both drive structures are carried by segment 14 and both clamping structures by segment 16.

It is also contemplated that a "half" finger motor 10 as depicted in FIGS. 1 through 4 of the drawings may be fabricated using only a single drive structure 32A and a single clamping structure 78A. Such an embodiment would operate like a water wheel or impulse wheel, with PZA 44A drive strokes and clamping of segment 16 to bushing 26A by PZA 90A being appropriately timed. While such an embodiment would lack the power of the preferred embodiment, it would be suitable for many applications.

Figure 27:
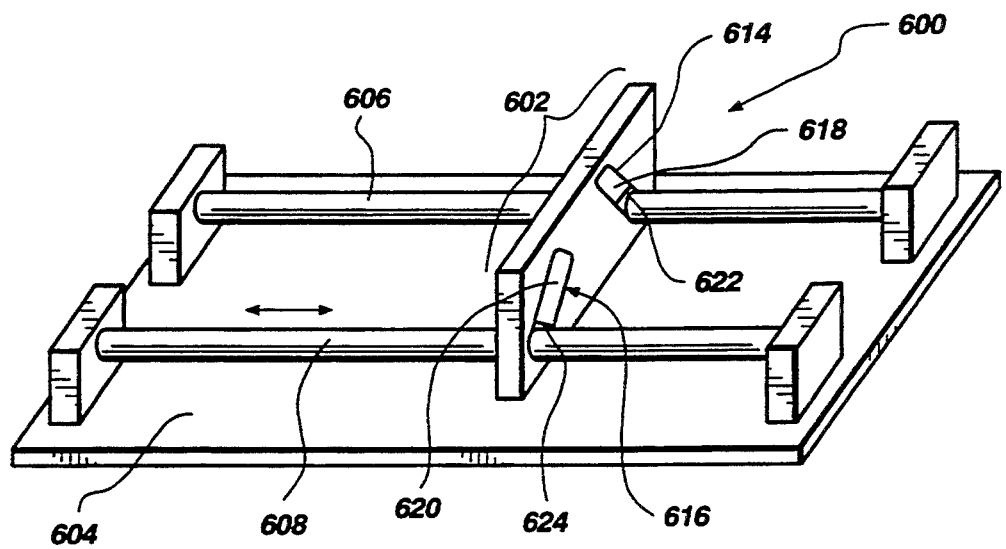
FIG. 27 is a schematic perspective of a linear finger motor.
Figure 28:
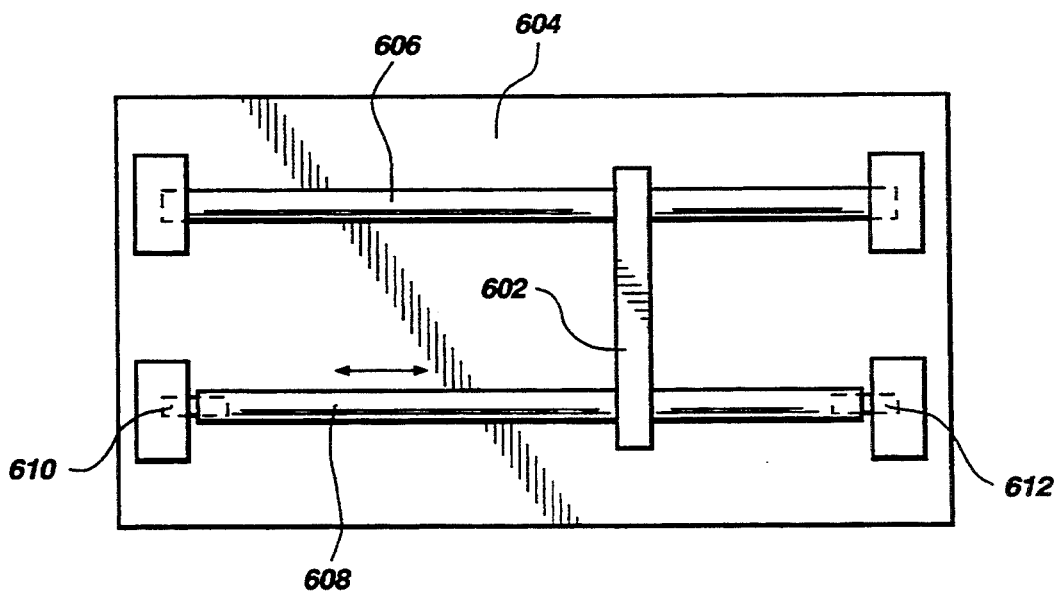
FIG. 28 is a top elevation of the linear finger motor of FIG. 27.

Yet another alternative embodiment of the finger motor is a linear motor, illustrated in FIGS. 27 and 28. In this embodiment, motor 600 provides linear translational movement of an element 602 relative to a supporting base 604. Base 604 has supported thereon a fixed cylindrical guide shaft 606 and a longitudinally oscillating or reciprocating drive shaft 608 extending parallel to guide shaft 606. PZA's 610 and 612 are positioned at respective ends of drive shaft 608, and are interposed between the shaft ends and supports secured to the base 604. Movable element 602 may comprise a plate having two clamping structures 614 and 616 driven by PZA's 618 and 620 acting on clamping shoes 622 and 624, clamping structure 614 having the ability to selectively lock element 602 to guide shaft 606 and clamping structure 616 having the ability to selectively lock element 602 to drive shaft 608.

Element 602 is moved by clamping same via clamping structure 616 to oscillating drive shaft 608 prior to the time the later moves longitudinally in the desired direction responsive to the timed energizing and de-energizing of PZA's 610 and 612, and releasing element 602 from drive shaft 608 at the end of its stroke in that direction substantially simultaneously and clamping element 602 to fixed guide shaft 606 via clamping structure 616 to prevent backward movement of element 602 as drive shaft 608 resets for another power stroke. Thus it is readily apparent that motor 600 operates in exactly the same manner as finger motor 10, only in a linear mode.

It will also be apparent that two or more oscillating parallel drive shafts 608 may be employed and that guide shaft 606 may in some instances be eliminated. With two drive shafts, power or drive strokes can be more frequently applied to element 602, increasing the potential speed thereof. Furthermore, it is contemplated that only a single PZA be employed per drive shaft, and a spring or other resilient member be placed at the opposite end to effect a "return" stroke of the shaft. Finally, two elements 602 may be employed in motor 600, and used as movable gripping jaws by appropriately timed locking and unlocking to one or more drive shafts 608 to move each element 602 in the desired direction.

Further with respect to finger motor embodiments, it is also contemplated that a finger motor having a segment 16 capable of continuous rotation rather than limited rotation through less than a 360° arc may be easily fabricated by using slip ring commutators to transmit electrical power to the clamping structure or structures (or drive structures) carried by the rotating segment.

B. Star Motor

The following text describes several embodiments of linear star motors and rotary star motors. Star motors are believed to have particular utility when employed in combination with rotating joints for robotic limbs, for extensible limbs, and for robotic hands having powerful grips. Such motors can possess a holding torque of about four times stall torque, and have a high positioning accuracy as small-increment stepper motors. They can be designed to be either self-braking or free-wheeling when power is lost, and in certain applications can be made highly redundant with only a small weight gain, so that if a particular drive set of a motor becomes inoperative, the motor is still able to function. The motors are very robust and very compact, being substantially two-dimensional with a very thin third dimension. Multiple stator assemblies may be stacked to even further enhance the torque applied to a common rotor without losing the compact character of the motor. Finally, the star motor is equally adaptable to rotary and to linear motion.

1. Linear Star Motor

Figure 11:
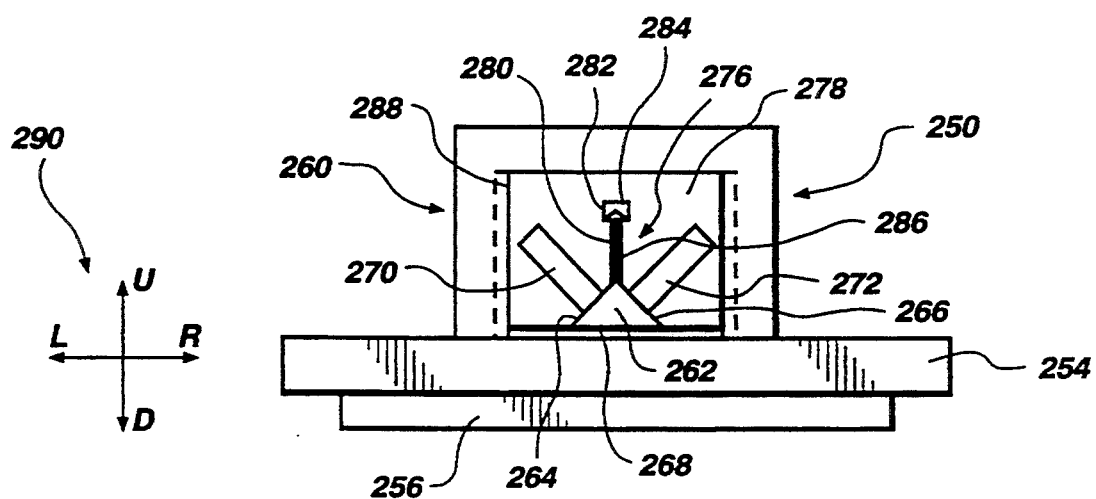
FIG. 11 is a side view of a first preferred embodiment of a V-drive linear star motor.

FIG. 11 shows a side view of a first preferred embodiment of a V-drive linear star motor 250. An element 254 to be driven, such as a metal rod, plate or strip, is supported by a support 256. A drive mechanism 260 includes a substantially triangular drive shoe 262, a PZA 270, a PZA 272, and a biasing structure 276, all assembled in a stator block 278, preferably a solid piece of metal. Drive shoe 262 includes upper surfaces 264 and 266 adjacent PZA's 270 and 272, respectively, and lower drive surface 268 which lies over element 254. PZA's 270 and 272 are each oriented at an oblique angle to element 254, defining a "V" shape. The included angle of the "V" should optimally be between 45° and 135°. The angle may vary depending upon whether motor speed or force is to be optimized, or a compromise achieved. For example, using a "narrow" V-drive with a small included angle and both PZA 270 and 272 oriented more perpendicularly with respect to element 254 will result in relatively higher forces being applied to element 254 through drive shoe 262 than if PZA 270 and 272 were oriented in a "wide" V, the latter configuration providing more displacement of element 254 per cycle of drive shoe 262, but at the expense of force.

Biasing structure 276 may include a Belleville washer 282 and music wire 280 attached to drive shoe 262, the former disposed in washer cavity 284 and the latter extending to shoe 262 through a slot or channel 286 in stator block 278, to pull drive shoe 262 away from contact with element 254. Upward biasing of drive shoe 262 may, of course, be provided by other arrangements, but the configuration disclosed is particularly simple and effective. When either of PZA 270 or PZA 272 is energized, it presses against drive shoe 262, which in turn presses against element 254. When neither PZA 270 nor PZA 272 is energized, biasing structure 276 pulls drive shoe 262 slightly away from element 254. Schematically depicted slide mechanism 288 may adjust the position of drive mechanism 260 up and down to accommodate elements 254 having widely differing thicknesses. Slide mechanism 288 may comprise a simple set screw lockable against ridges on stator block 278 received in channels in support structure 256, or may comprise a precise gear-type adjustment with micrometer settings, or even comprise another star motor drive unit acting on stator block 278 in a direction perpendicular to element 254. If the only adjustment required is to accommodate dimensional tolerances of similar elements 254, a simple adjustment set screw threaded into stator block 278 and being on the upper ends of PZA 270 and 272 and longitudinally aligned therewith may be employed for this purpose, as such may be included in any case in motor 250 to assist in the proper loading of drive shoe 262 by PZA's 270 and 272.

Figures 12, 12A:
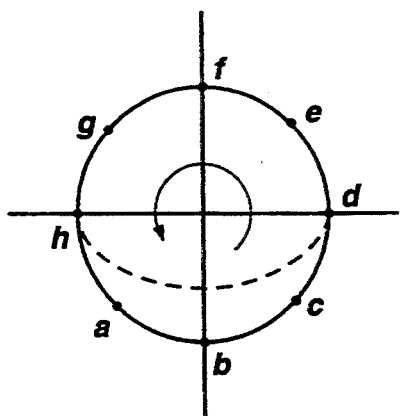
FIG. 12 is a graphic illustration of the actuator operating sequence of the V-drive linear star motor of FIG. 11.
FIG. 12A is a graphic illustration of the drive shoe positions of the star motor of FIG. 11, corresponding to the actuator operating sequence depicted in FIG. 12.
Figure 17:
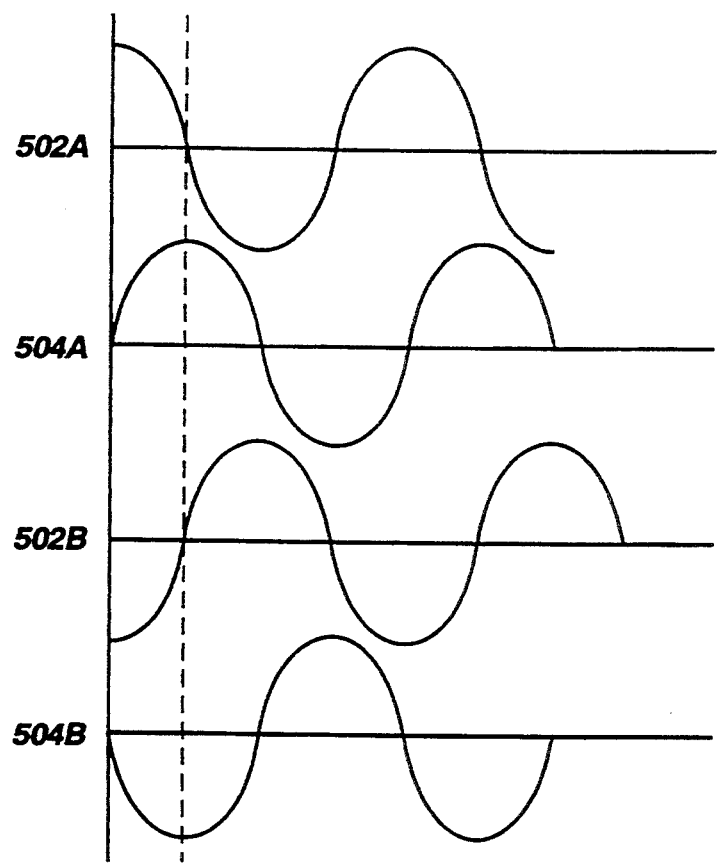
FIG. 17 depicts the phased sine wave signals employed in a two-phase drive for the star motor of FIGS. 15 and 16.

FIGS. 12 and 12A graphically depict the operation of V-drive linear star motor 250, FIG. 12 depicting the energization states of PZA 270 and PZA 272 as driven by phased sine waves as depicted in FIG. 17. "E" indicates a PZA is energized, and "NE" that it is not energized. Fractions next to an "E" indication set forth the approximate degree of energization due to the sine wave drive signal. FIG. 12 also depicts the direction of movement of drive shoe 262 and of element 254 corresponding to the energization states of PZA's 270 and 272, the directions being keyed into those indicated in FIG. 11. "NM" indicates no movement of an object. FIG. 12A depicts the generally circular nature of the trajectory of drive shoe 262, and letters "a" through "h" indicate different positions of drive shoe 262 which, by like letters "a" through "h" at the top of FIG. 12, are shown to correspond to the different energization states of PZA's 270 and 272 for times $t_0$ through $t_8$. The broken line in FIG. 12A depicts a flattened, more ellipsoidal trajectory resulting from contact of drive shoe 262 with element 254. It should be noted that the biasing structure associated with motor 250 causes some movement of the drive shoe 262, and that effect has been accounted for in FIGS. 12 and 12A. Moreover, it should be noted that the phase relationship between the motor drive signals can be modified to create a more ellipsoidal drive shoe trajectory, with the long axis of the ellipse oriented as desired. It should also be noted that the angles of drive shoe faces 264 and 266 as well as the included angle between PZA's 270 and 272 will also affect the trajectory of drive shoe 262.

Figures 13, 14:
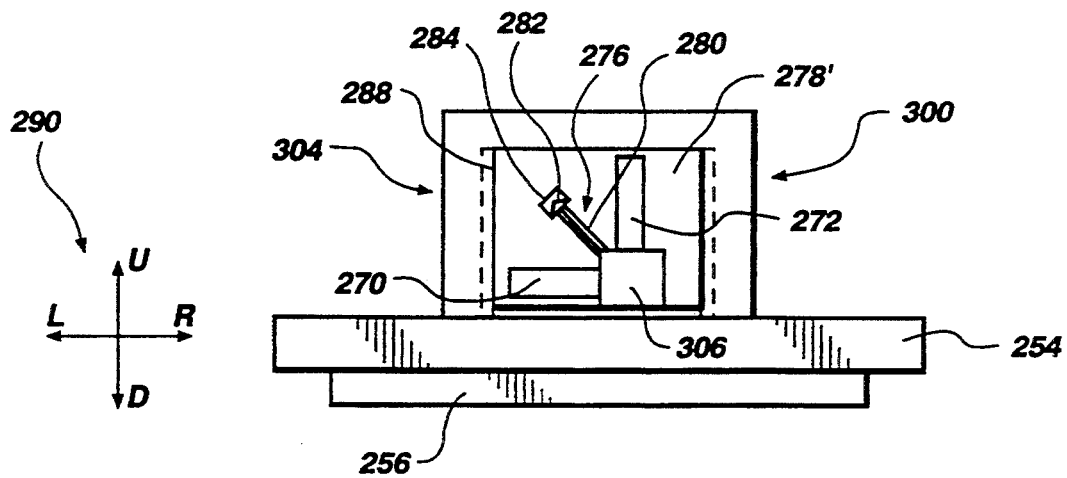
FIG. 13 is a side view of a first preferred embodiment of an L-drive linear star motor.
FIG. 14 is a graphic illustration of the actuator operating sequence of the L-drive linear star motor of FIG. 13.

FIG. 13 shows a side view of a first preferred embodiment of an L-drive linear star motor 300. Elements of motor 300 which are the same as those of motor 250, are numbered the same. Driven element 254 is again supported by a support 256. A drive mechanism 304 includes a drive shoe 306, a PZA 270, a PZA 272, and a biasing structure 276, all assembled in a stator block 278. Drive shoe 306 is preferably rectangular or square shaped. PZA 270 is oriented parallel to the orientation of driven element 254, while PZA 272 is oriented perpendicular thereto. In the L-drive motor, when PZA 270 is energized it moves drive shoe 306 to the right. When PZA 272 is energized, it moves drive shoe 306 down until it firmly presses against element 254. When neither PZA 270 nor PZA 272 is energized, biasing structure 276 pulls drive shoe 306 slightly away from element 254. Thus, a substantially triangular drive shoe trajectory is provided. A slide mechanism 288 permits adjustment of drive mechanism 304 up and down to accommodate driven elements of significantly different thicknesses.

FIG. 14 graphically illustrates the operation of L-drive linear star motor 300. FIG. 14 uses the same symbols as were used in FIG. 12 with respect to energization of the PZA's, the movement directions of drive shoe 262 and element 254 are keyed to FIG. 13, and "NM" indicates no movement of an object. From time $t_0$ to time $t_1$, both PZA 270 and PZA 272 are de-energized and drive shoe 306 does not engage element 254 with any significant force. From time $t_1$ to time $t_2$, PZA 270 is de-energized and PZA 272 is energized, moving shoe 306 downward until it firmly engages object 254. From time $t_2$ to time $t_3$, PZA's 270 and 272 are energized, the former moving drive shoe 306 to the right, which in turn moves element 254 to the right. From time $t_3$ to time $t_4$, PZA's 270 and 272 are de-energized and biasing structure 276 returns drive shoe 306 upward and to the left to its original position. From time $t_4$ to time $t_5$, PZA 270 is de-energized and PZA 272 is energized, moving shoe 306 downward until it again firmly engages element 254. From time $t_5$ to time $t_6$, PZA's 270 and 272 are energized, moving drive shoe 306 to the right, which in turn moves element 254 to the right. The durations between times are not necessarily equal. For example, the time between times $t_2$ and $t_3$ is not necessarily the same as the time between times $t_3$ and $t_4$. If it is desired to reverse the direction of motor 300, the energizing sequence of PZA's 270 and 272 is altered so that element 254 is contacted by shoe 306 as it is retracted to the left by biasing structure 276.

2. Rotary Star Motor

Figure 15:
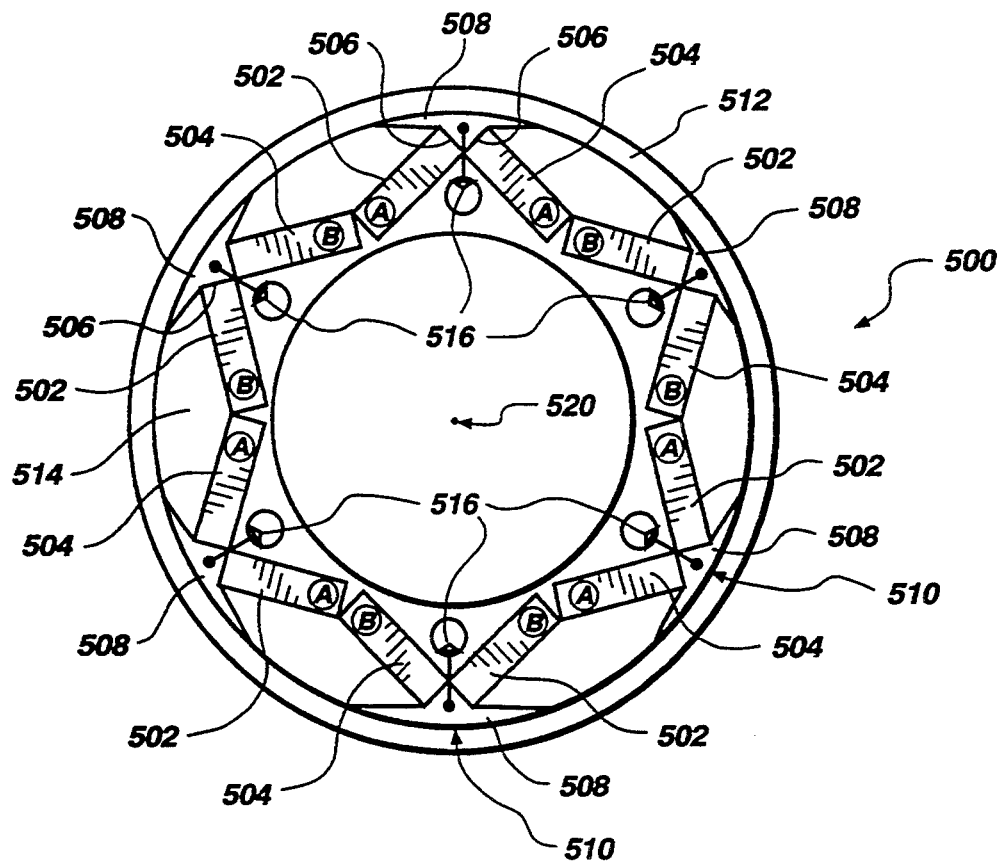
FIG. 15 is a side or plan elevation of a rotary star motor employing a V-drive.

Referring to FIG. 15 of the drawings, a V-drive rotary star motor 500 is illustrated with the rotor disk, shaft and bearing assembly omitted for clarity. Motor 500 includes multiple drive assemblies comprising pairs of PZA's 502 and 504 oriented at a mutual included angle of substantially 90° the drive faces of PZA's 502 and 504 each abutting load faces 506 of drive shoes 508, the outer arcuate surfaces 510 of which engage the I.D. of rotor 512 disposed about stator assembly 514, which carries the drive assemblies. As with the previously described linear star motors, rotary star motor 500 biases each drive shoe 508 in tension by suitable biasing structures 516. The energization sequence for the paired PZA's is the same as previously described with respect to the linear V-drive star motor, and as illustrated in FIG. 12 of the drawings.

Figure 16:
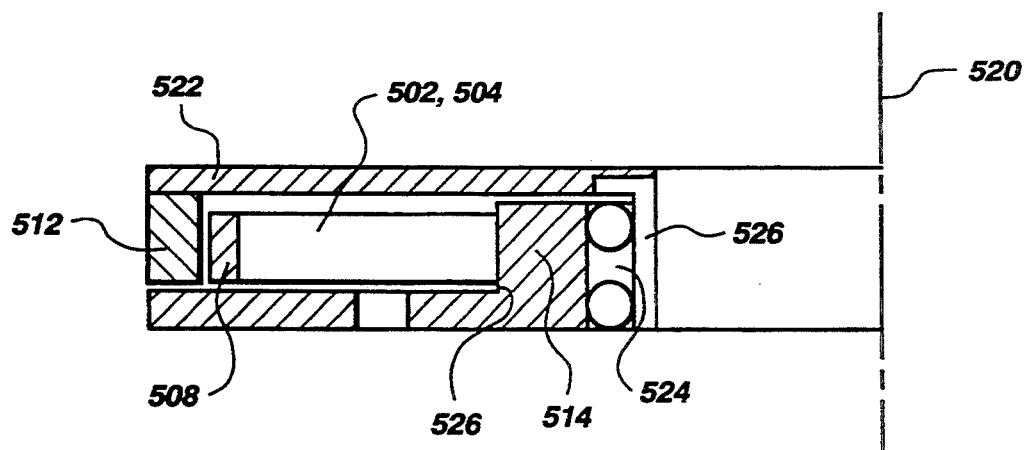
FIG. 16 is a partial side sectional elevation of the rotary star motor of FIG. 15.

FIG. 16 depicts a side sectional elevation of motor 500 of FIG. 15, taken from the center line 520 of motor 500 and showing the rotor disk 522 overlying and secured to the rotor rim 512 and bearing 524 by which rotor shaft 526 and thus the entire rotor is free to rotate with respect to stator assembly 514. FIG. 16 also shows a layer of Teflon ® (tetrafluoroethylene) sheeting or other friction-reducing material 526 under PZA 502, 504, which layer reduces friction between the rapidly expanding and contracting PZA's and stator assembly 514. It is also desirable that the sides of the cavities in stator assembly 514 which receive PZA's 502 and 504 also be lined with Teflon ® or other friction-reducing material to facilitate expansion and contraction of the PZA's and lessen wear and friction-induced heating of the motor.

All of the pairs of PZA's may be driven in single phase, but it is preferred to operate alternate pairs of PZA's out of phase so as to achieve smoother movement of rotor 512 and lower noise levels. It is further contemplated that more phases be employed. For example, in a six-drive assembly motor as depicted in FIG. 15, each of the drive assemblies may be driven in different phases to provide smooth torque output, in contrast to operating all six drive assemblies in phase, which would provide a great deal of force but a substantial torque ripple from the motor. This ability to change motor output characteristics of a multiple drive assembly motor by varying the drive signal phasing provides significant flexibility to address a variety of operating requirements. As with the shoes of the linear V-drive star motor, shoes 508 of motor 500 translate in a circular or ellipsoidal path, and reversal of rotor direction or rotation is achieved by simply reversing the PZA energization sequence.

FIG. 17 of the drawings depicts the sinusoidal voltage waveform timing preferably employed for rotary star motor 500 for two-phase activation of the PZA's, the paired PZA's being identical as either "A" phase or "B" phase in both FIGS. 15 and 17.

It is, of course, possible to fabricate an L-drive rotary star motor, the details of which will be apparent from the previous description of the linear L-drive motor. The L-drive may possess several advantages over the V-drive in a rotary star motor configuration, including compactness, so that more actuator pairs may be employed for a given motor diameter. In addition, the L-drive tangential PZA may be smaller than the PZA's employed in the V-drive embodiment as the former is aligned with the direction of rotor element movement and thus needs only to produce a force equal to the radially applied force of the normal PZA times the coefficient of friction between the drive shoe 508 and the normal PZA, in contrast to the V-drive embodiment wherein each PZA produces a radially and tangentially applied force and there is frictional sliding contact between the inner drive shoe surfaces and both PZA's.

As with the other embodiments of the present invention, the rotary (and linear) star motors may be fabricated without the use of exotic materials and at a reasonable cost. The stator assembly body may be aluminum machined into a disk and having channels milled therein to accept PZA's. As noted above, the PZA channels are lined with Teflon strips, and a thin aluminum retention plate, also having appropriately placed Teflon straps adjacent PZA's, is secured over the stator with screws. The drive shoes may be aluminum, anodized aluminum, steel, tungsten carbide, aluminum bronze, ceramics or other wear-resistant materials known in the art. The biasing structure may comprise music wire tensioned by one or more Belleville washers or other spring means. The rotor shaft may be steel, as may the rim, both being secured to an aluminum rotor disk. Alternatively, the rotor rim, disk and shaft may comprise a single piece.

3. Alternative Configurations and Applications of Star Motors

Figure 18:
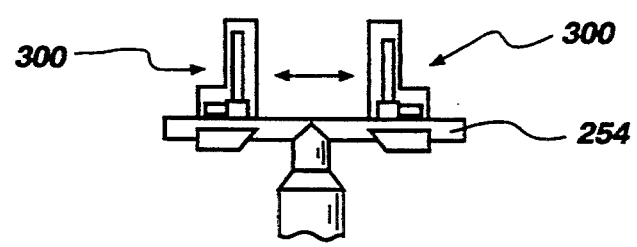
FIG. 18 is a schematic side elevation of two L-drive star motors configured as a robotic gripper.
Figure 18A:
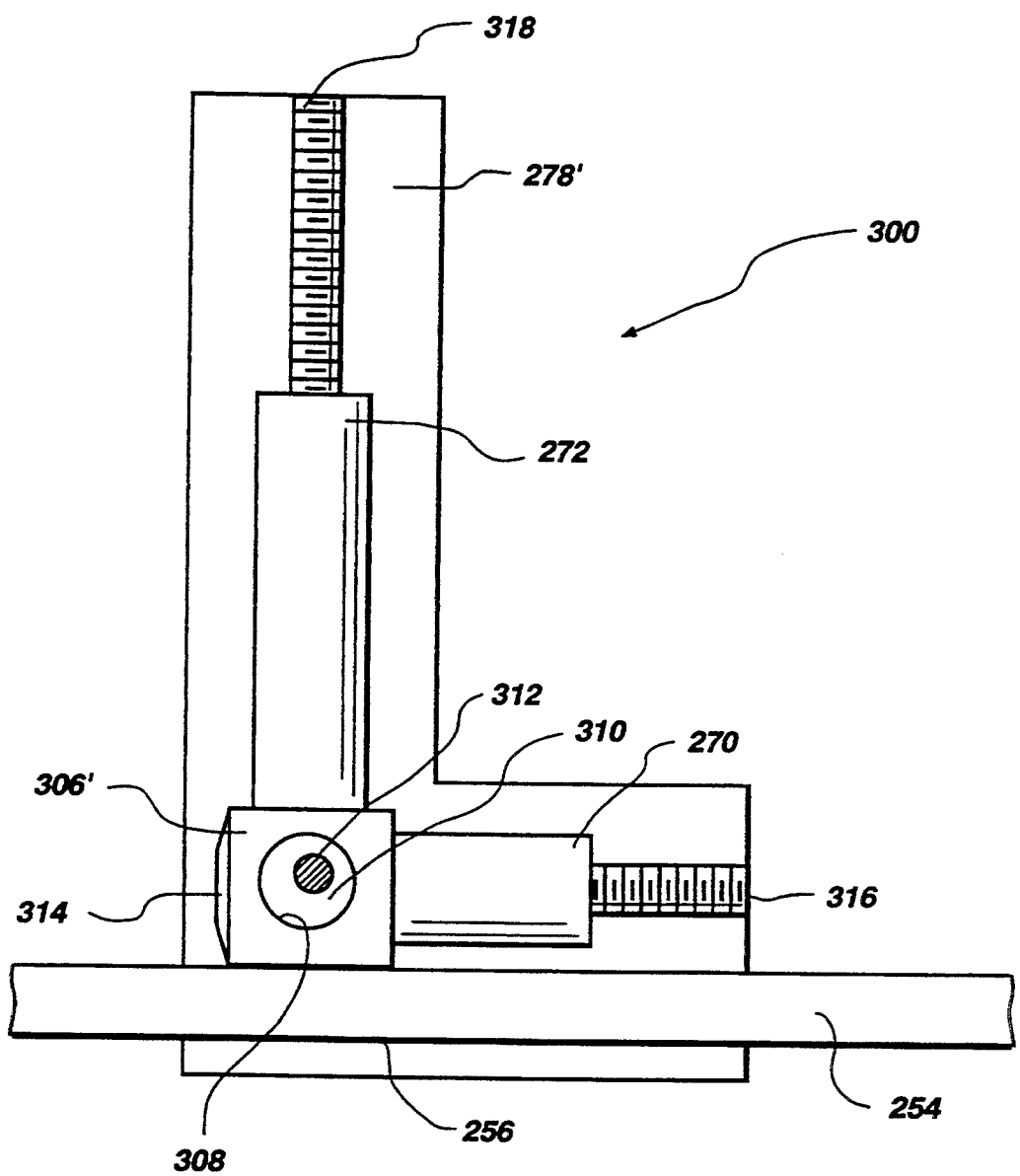
FIG. 18A is an enlarged side elevation of the right-hand star motor depicted in FIG. 18.
Figure 19:
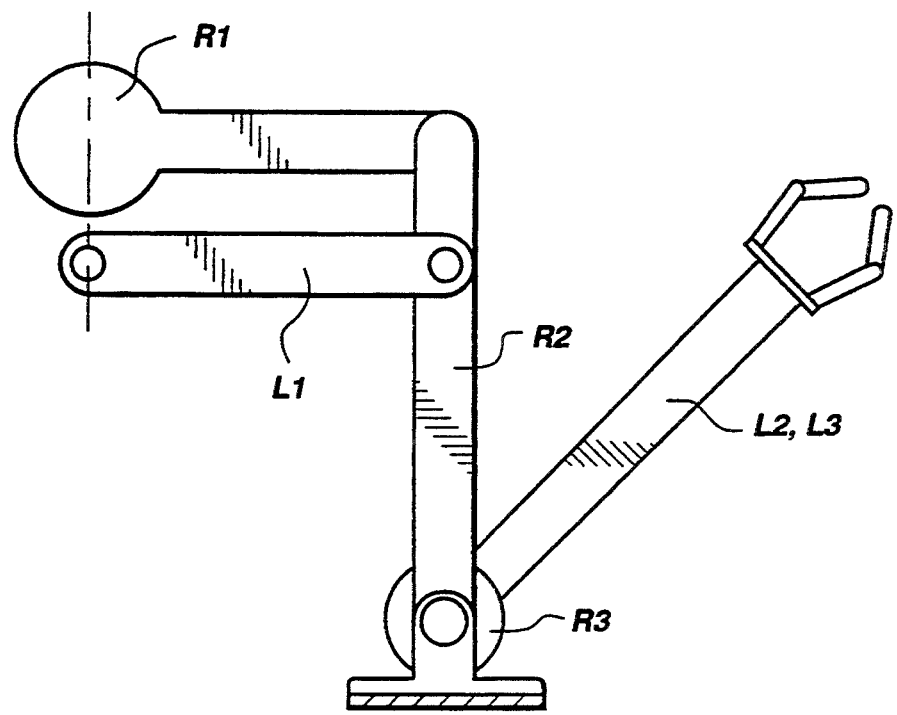
FIG. 19 is a schematic side elevation of a prehensile robotic leg employing multiple star motors.

It will be readily appreciated by those of ordinary skill in the art that the star motors admit to a variety of diverse applications. For example, as shown in FIG. 18, two L-drive motors 300 may be mounted on a straight bar and each function as a jaw of a robotic gripper. L-drive motors are preferred for their aforementioned compactness, although a V-drive gripper could also be fabricated. FIG. 18A is an enlarged view of right-hand L-drive motor 300.

L-drive motor 300 of FIG. 18A includes PZA's 270 and 272 carried in a stator block 278' and acting on a modified rectangular drive shoe 306' which moves stator block 278' on bar 254. Drive shoe 306' includes an aperture 308 therethrough having a resilient element 310 set therein, and a screw, bolt or rod 312 extending through resilient element 310 and secured to stator block 278 (securing means not shown) to pre-load resilient element 310 and provide a bias upwardly and to the right for drive shoe 306'. Disk spring 314 may also be employed to bias drive shoe 306'. Adjustment set screws 316 and 318, previously referenced with respect to other embodiments of the star motor, are shown in FIG. 18A. Support 256 may include on its upper surface a friction-reducing coating to facilitate movement of stator block 278' on bar 254. FIG. 18A is thus illustrative of other and further variations of the L-drive motor of the present invention.

As noted above, multiple stators may be employed with a single rotor in the rotary star motor, to multiply torque. The stators may be joined or separate, and drive separate or a common rotor. The rotors may be driven on their O.D.'s if desired, with the PZA's and drive shoes facing readily inward or rotors may be driven on both their I.D.'s and O.D.'s. Rotors may also comprise disks rather than rings, and the PZA drive assemblies may be oriented at an angle to the disk plane and act upon the rotor disk surface. Seals may be employed between the rotor rim and the stator to prevent particulate intrusion. Various types of bearings may be employed, and a solid lubricant such as molybdenum disulfide is preferred.

Figure 20:
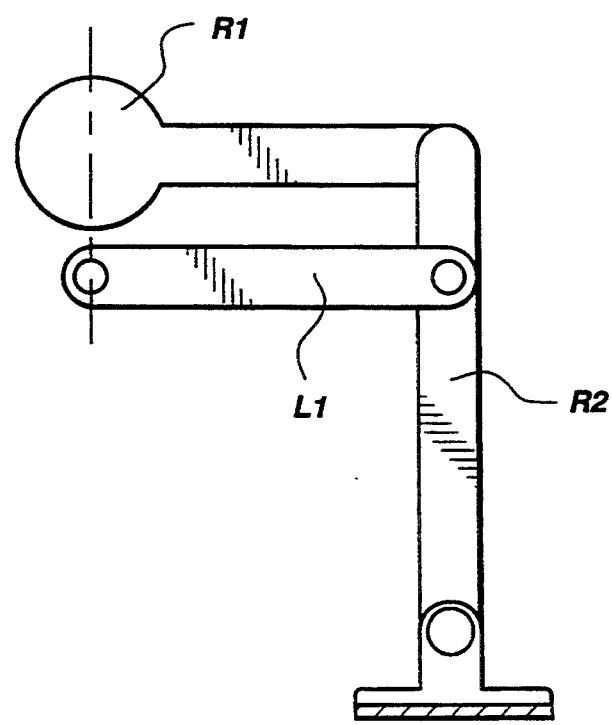
FIG. 20 is a schematic side elevation of a normal robotic leg employing multiple star motors.
Figure 21:
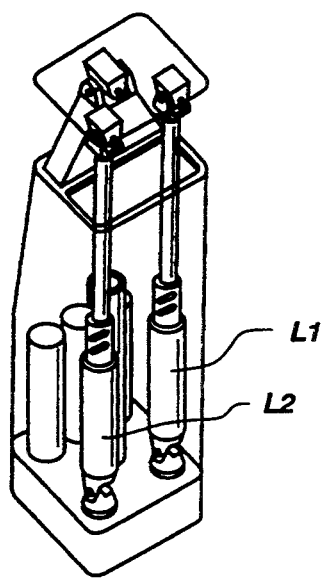
FIG. 21 is a schematic perspective view, partially in phantom, of a robotic wrist employing linear star motors for pitch and yaw control.
Figure 22:
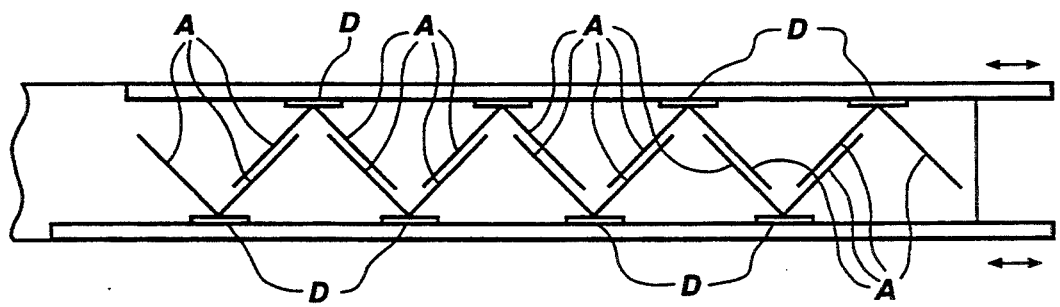
FIG. 22 is a schematic side elevation of a compact tandem linear star motor arrangement having utility in the robotic wrist of FIG. 21.
Figure 23:
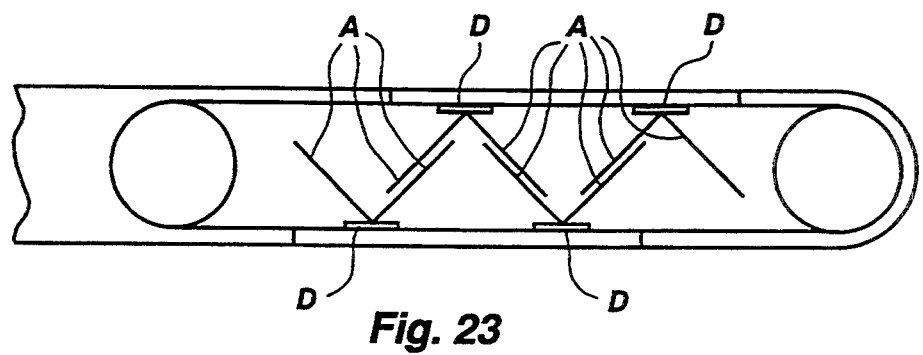
FIG. 23 is a schematic side elevation of a compact tandem linear star motor arrangement for robotics foot rotation.
Figure 24:
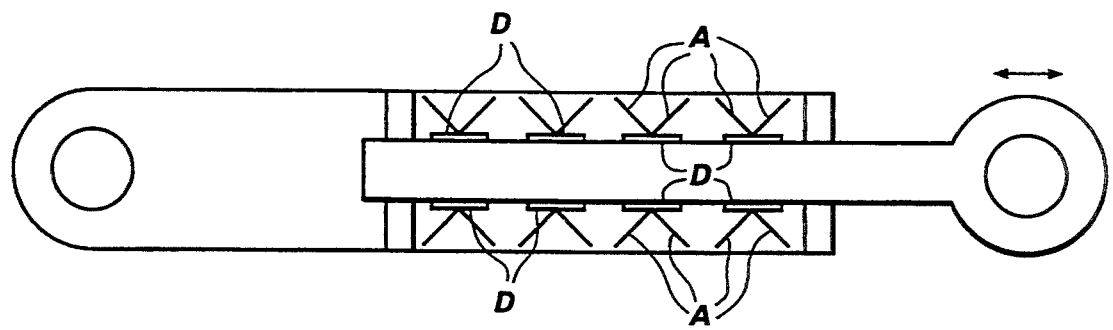
FIG. 24 is a schematic side elevation of a high power tandem star motor in an "X" drive configuration, for driving an extensible robotic thigh.

FIGS. 19-24 schematically depict various robotics applications for rotary and linear star motors employing actuators A and drive shoes D. The device of FIG. 19 employs three rotary motors R1-R3 and three linear motors L1-L3 in a prehensile leg, which may also employ finger motors in the "hand" at the end of the forearm. FIG. 20 depicts a normal leg using two rotary motors R1-R2 and a single linear motor L1. If desired, a small rotary star motor may be employed in the robot "ankles" of FIG. 19 to provide the forearm with the ability to rotate at its base about a vertical axis. FIG. 21 depicts a robotic wrist design employing two linear star motors L1 and L2 for wrist pitch and yaw control. FIG. 22 depicts staggered parallel, overlapping outwardly facing rows of linear star motors, which may be used in configurations requiring compactness for the pitch and yaw control in the robotic wrist of FIG. 21. FIG. 23 depicts a staggered, parallel, overlapping outward facing rows of linear star motors employed as a robotic foot rotation motor, for example as motor R2 in FIGS. 19 and 20. It should be noted in FIG. 23 that the rotor element may comprise a flexible strip or band. FIG. 24 depicts an "X" drive star motor, with parallel, inwardly facing rows of linear star motors used to extend and retract a robotic thigh. Of course, many other combinations of rotary and linear star motors are possible, and many also are used in combination with the previously-described finger motors and the subsequently-described ratchet motors.

Figure 29:
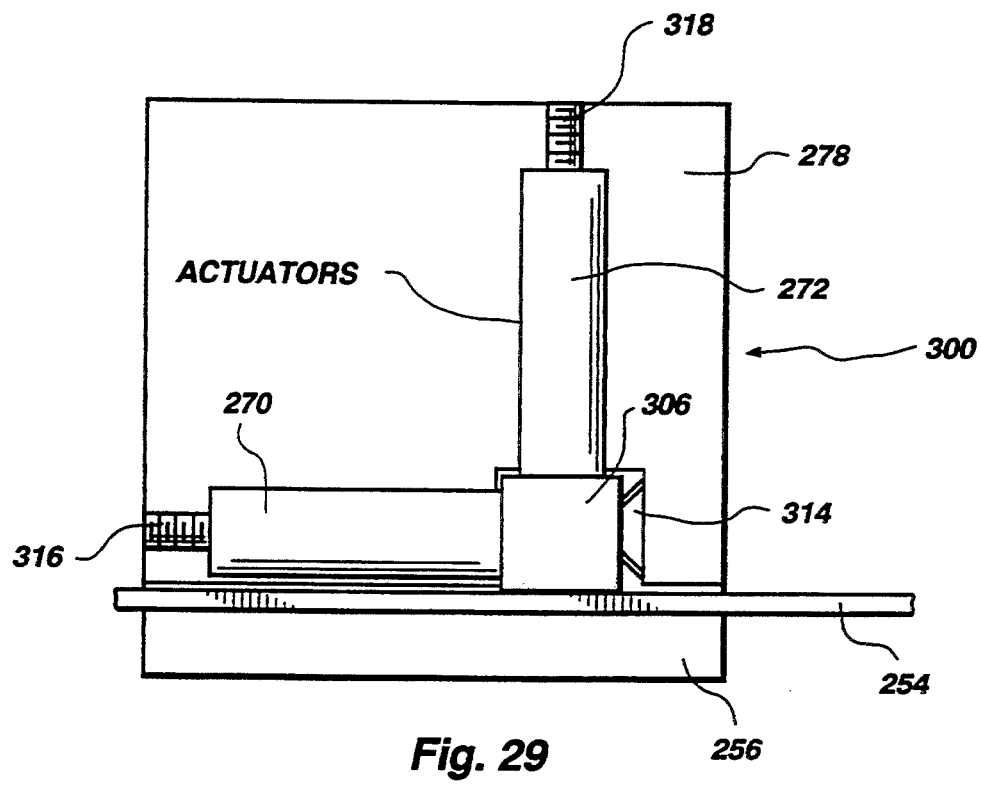
FIG. 29 is a side elevation of an alternative L-drive linear star motor configuration.

FIG. 29 depicts a modified L-drive linear star motor 300 employing only a disc-type shoe return spring 314 in lieu of the biasing arrangements previously described.

Figure 30:
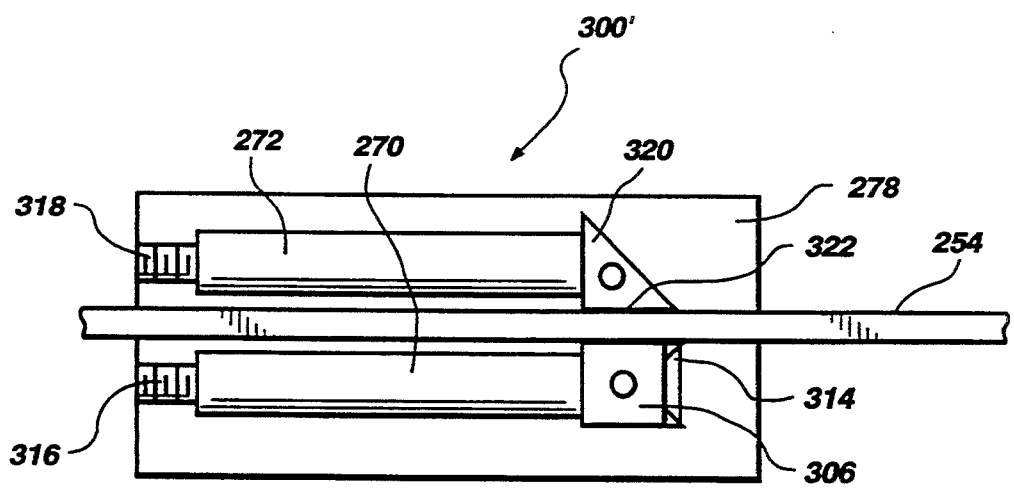
FIG. 30 is a side elevation of a parallel-drive alternative linear star motor according to the present invention.

FIG. 30 depicts a parallel-drive linear star motor 300' wherein normally perpendicular PZA 272 is oriented parallel to element 254 to conserve space, PZA 270 is disposed under element 254 and a clamping effect to ensure firm contact of drive shoe 306 with element 254 is achieved with clamping wedge 320. In this embodiment it is desirable to coat or cover the element-contacting face of clamping wedge 320 with a friction-reducing material 322.

Figure 31:
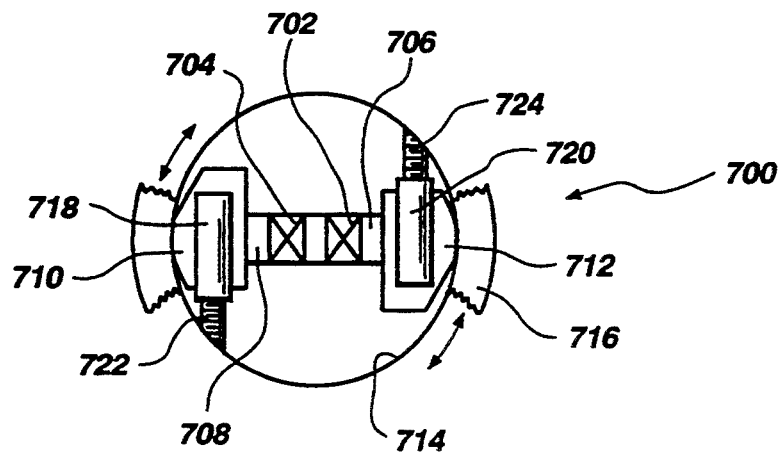
FIG. 31 is a top schematic elevation of a modified, compact L-drive rotary star motor according to the present invention.
Figure 32:
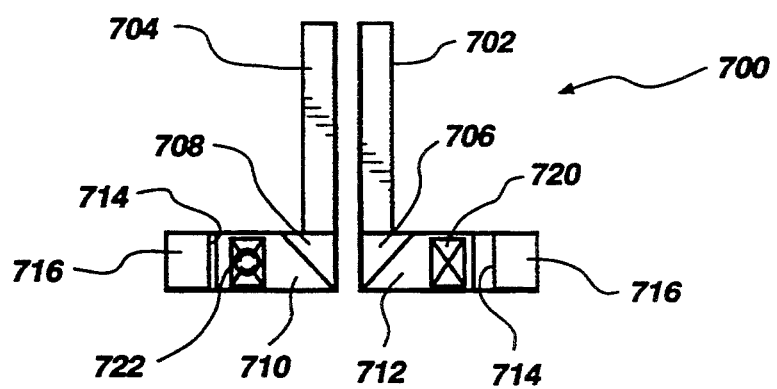
FIG. 32 is a side schematic elevation of the motor of FIG. 31.

FIGS. 31 and 32 depict yet another modification of an L-drive star motor which in some respects is similar to the motor of FIG. 30 and in some respects similar to the previously-described finger motor in that the motor of FIGS. 31 and 32 employs a clamping structure. Motor 700 includes clamping PZA's 702 and 704 which act on clamping wedges 706 and 708 to move drive shoes 710 and 712 outwardly against the inner rim 714 of a rotor structure 716 at appropriately timed intervals as drive PZA's 718 and 720 are periodically energized to move drive shoes 710 and 712 substantially tangentially to inner rim 714 and thus cause rotor structure 716 to rotate. Adjustment set screws (such as 722, 724 shown) are employed to ensure firm contact of the PZA's with the elements they act upon. If desired, resilient return members may be added at appropriate locations to motor 700 to reset drive shoes 710 and 712 when PZA's 718 and 720 are de-energized, and to reset clamping wedges when PZA's 702 and 704 are de-energized. It may further be desirable to add a friction-reducing material between the clamping wedges and the drive shoes, and around the PZA's, to facilitate expansion and contraction thereof.

While the star motors described above have been single-degree of freedom motors wherein rotor elements move in a single linear or arcuate path, the invention is not so limited. Motors wherein a rotor element rod is moved linearly and also rotated about its axis by an appropriately shaped drive shoe are clearly possible, and contemplated as within the scope of the invention. Similarly, a sheet or plate-type rotor element may be moved in any direction in its plane by appropriate orientation of several PZA-drive assemblies, such as one at an "X" direction and one in a "Y" direction at 90° to the "X" direction, movements in other directions in the plane being achievable by combined actuation of the two (or more) dissimilarly oriented drive assemblies.

C. Ratchet Motor

Figure 25:
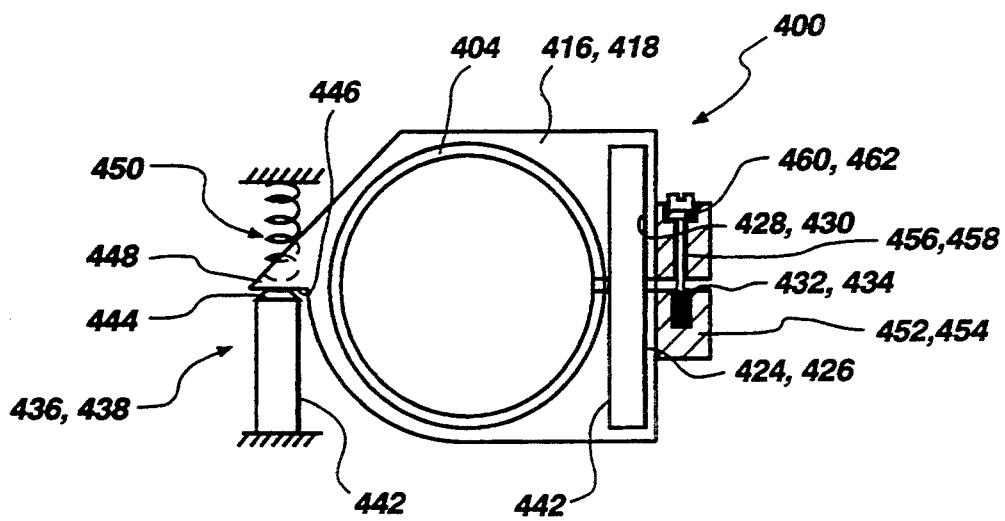
FIG. 25 is a schematic side elevation of a preferred ratchet motor embodiment of the present invention.
Figure 26:
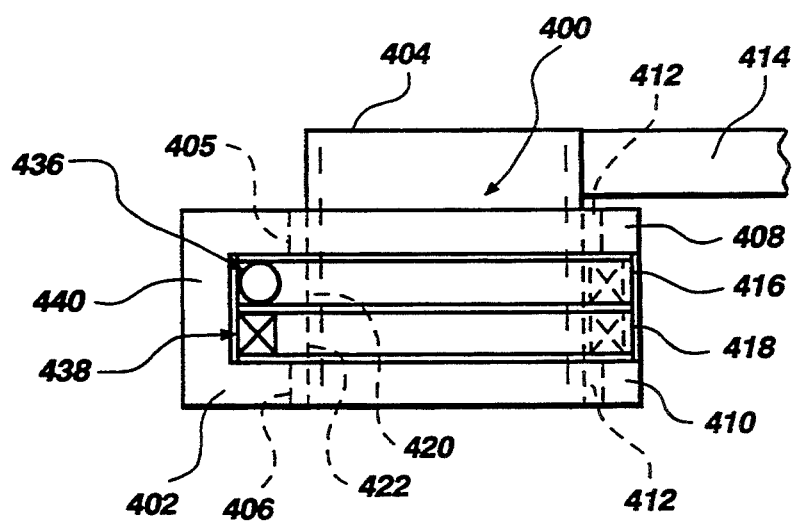
FIG. 26 is a schematic top elevation of a preferred ratchet motor embodiment of the present invention.

Referring now to FIGS. 25 and 26 of the drawings, a ratchet motor 400 according to the present invention is schematically depicted in side elevation and top elevation, respectively. Ratchet motor 400 comprises a stator assembly 402 supporting a rotor 404, which extends through aligned bushing cavities 405, 406 in the two legs 408, 410 of stator assembly 402. Rotor 404 is supported in each bushing cavity 405, 406 by circular bushings 412 so that it may freely rotate and resist cocking or jamming under uneven or offset application of loads, such as might be experienced if ratchet 400 motor is employed to rotate the "wrist" or "thigh" of a robotic limb to the side, in a motion which may be termed "yaw". In such a robot, stator assembly 402 would preferably be secured to or be part of the robot torso, and rotor 404 secured to an arm or leg element or limb 414 of the robot.

Two split-ring clamping assemblies 416, 418 having clamping apertures 420, 422 therethrough are disposed within the legs 408, 410 of stator assembly 402 and about rotor 404. The inner diameter (I.D.) of clamping apertures 420, 422 is less than the outer diameter (O.D.) of rotor 404 when clamping assemblies 416, 418 are in a relaxed, unstressed state. PZA 424 and PZA 426 are disposed in cavities 428 and 430, respectively, in clamping structures offset from and in substantially tangential orientation to rotor 404, bridging slits 432, 434 in clamping assemblies 416, 418. When PZA 424 or 426 is energized, it expands its respective clamping assembly to permit relative rotation of rotor 404. When the PZA is de-energized, the clamping assembly locks onto rotor 404 due to the elastic nature of the clamping assembly material. The split-ring clamping assemblies may be analogized to the oscillating clamping structures of the finger motor embodiment.

Stator assembly 402 houses at least one, but preferably two, oscillating drive assemblies 436, 438 proximate the base 440 of the assembly. Drive assemblies 436, 438 each comprise a PZA 442 having a drive shoe 444 which bears against radially aligned (with respect to rotor 404) outwardly extending drive surface 446 of drive tab 448 on a clamping assembly 416 or 418 (see FIG. 25). Opposing and longitudinally aligned with PZA 442 is resilient return member 450, which may comprise a coil spring, elastomeric element, one or more Belleville springs, or one or more leaf springs, as desired. If it is desired to effectuate rapid, substantially continuous motion of rotor 404, two drive assemblies may be employed, either oriented in the same manner or in opposing orientations (with one of the clamping assemblies reversed) so as to provide a positive drive via a PZA in each direction of rotation. A single PZA may, of course, be employed, and the stored energy of component return member 450 be employed to rotate rotor 404 as described with respect to the finger motor. It is also contemplated that three, four or more drive assemblies may be "stacked" as with the star motor drives, and driven in multiple phases if desired for a smoother torque output and/or higher speeds.

In addition to the inherent resiliency of split-ring clamping assemblies 416, 418, the assemblies 416, 418 may also optionally include protrusions 452, 454 (see FIG. 25) which accommodate adjustable, threaded compression rods 456, 458. Compression rods 456, 458 are acted upon by one or more Belleville washers 460, 462 (or other suitable biasing means) to provide additional clamping force for locking clamping assemblies 416, 418 to rotor 404 when PZA's 424, 426 are de-energized. Adjustment of the force is provided by making up or backing off the threaded compression rods 456, 458. Of course, other structures may easily be adapted to provide additional clamping force, if desired or required by the application of the motor.

As with the finger motor, the appropriate timing of the clamping and release modes of clamping assemblies 416, 418 in combination with the timed energization of one or more PZA's employed in one or more drive assemblies 436, 438 will result in rotation of rotor 404 when a clamping assembly which is released by its PZA to grip rotor 404 is rotated by a drive PZA 442.

Described another way, the ratchet motor with two drive PZA's operates in a fashion similar to a familiar exercise for strengthening the wrists. In this exercise, a section of a broom handle is used with a rope fastened to the center of the handle and a weight attached to the other end of the rope. The exercise consists of grasping an end of the broom handle in each hand and turning it in order to lift the weight by winding up the rope on the broom handle. This is achieved through the following sequence of events.

1. Tightening the grasp of the right hand while releasing the left hand's grip.
2. Rolling the right wrist backward, toward the body.
3. Tightening the grasp of the left hand while releasing the right hand's grip.
4. Rolling the left wrist backward while rolling the right wrist forward, back to its original position in step 1.

The alternative clamping, rotating, releasing, and returning action is repeated the requisite number of times. Rotary motion in the opposite direction is simply achieved by reversing the phasing of the grasps.

Control circuitry for driving ratchet motor 400 is similar to that employed in the finger motor, and again may be easily fabricated from commercially available integrated circuit components by one of ordinary skill in the art. The drive signals, as with the finger motor, may be square, rectangular, triangular or other suitable waves, appropriately timed. As with the finger motor, the clamping PZA's are either energized or de-energized, and do not require any particular signal.

Suitable materials for the ratchet motor have also been previously discussed, and so will not be reiterated. The PZA's may be of the type previously described, sized to accommodate the desired force and rapidity of movement.

It has been previously noted that certain embodiments of the invention, when incorporated into various structures such as robotic hands, limbs, etc. may be made to become flexible or "go limp" upon de-energization. Such a capability is contemplated for all of the illustrated embodiments, and others, of the invention, just as is the ability to lock motor segments or components in position and to cause the structure to go rigid upon energization of actuators, for the purpose of clamping, locking or braking, as appropriate to the application of the motor.

While the field actuator motors of the present invention have been described with reference to certain preferred and alternative embodiments, the invention is not so limited, and many additions, deletions and modifications will be apparent to those of ordinary skill in the art and may be implemented without departing from the spirit and scope of the invention as hereinafter claimed.

For example, many rotor element shapes may be employed, as well as rotor elements which are flexible in one or more planes. Actuators may be placed in side-by-side relationships to act upon larger drive shoe surfaces. Different types and shapes of field actuators may be combined in a single motor. Various embodiments of the motor of the present invention, and components thereof, may be combined in various ways to obtain yet other embodiments within the scope of the invention.

What is claimed is:

1. A motor, comprising:
    a stator member carrying a first field actuator drive means adapted to vary in at least one dimension responsive to application or removal of an energy field;
    a rotor element hinged to said stator member and rotatably movable about said hinge with respect to said stator member;
    a first drive shoe in contact with said first field actuator drive means, adjacent said rotor element and movable responsive to said dimensional variance of said first field actuator to effect rotational movement of said rotor element relative to said stator member; and
    an energy source for providing a said energy field.

2. The motor of claim 1, wherein said hinge includes a pin fixed to said stator member and said motor further includes a rotary drive element mounted on said pin, said rotary drive element includes a first drive surface located adjacent said first drive shoe, said rotary drive element is rotatable from a first position to a second position responsive to contact of said drive surface by said first drive shoe, and said rotor element has associated therewith a clamping structure for selectively clamping said rotor element to said rotary drive element.

3. The motor of claim 2, further including means for returning said rotary drive element from said second position to said first position in the absence of said first field actuator drive means dimensional variance.

4. The motor of claim 3, wherein said means for returning said rotary drive element to said first position comprises biasing means.

5. The motor of claim 3, wherein said means for returning said rotary drive element to said first position comprises a second field actuator drive means adapted to vary in at least one dimension responsive to application or removal of an energy field, a second drive shoe in contact with said second field actuator drive means, and a second drive surface on said rotary drive element.

6. The motor of claim 2, wherein said clamping structure includes a first field actuator clamping means adapted to vary in at least one dimension responsive to application or removal of an energy field, and a first clamping shoe in contact with said first field actuator clamping means and adjacent said rotary drive element for clamping said rotor element to said rotary drive element.

7. The motor of claim 6, further wherein said clamping structure further includes a second field actuator clamping means adapted to vary in at least one dimension responsive to application or removal of an energy field and a second clamping shoe in contact with said second field actuator clamping means for immobilizing said rotor element with respect to said stator member.

8. The motor of claim 1, wherein said first field actuator drive means comprises a piezoelectric actuator, and said energy field comprises a voltage signal.

9. The motor of claim 1, wherein said first field actuator drive means comprises an electrostrictive actuator and said energy field comprises an electric field.

10. The motor of claim 1, wherein said first field actuator drive means comprises a magnetostrictive actuator and said energy field comprises a magnetic field.

11. A motor, comprising:
a stator member carrying a first field actuator drive means adapted to vary in at least one dimension responsive to application or removal of an energy field;
a rotor element movable with respect to said stator member;
a first drive shoe in contact with said first field actuator drive means and movable responsive to said dimensional variance of said first field actuator;
an energy source for providing a said energy field;
a rotary drive element associated with said rotor element, said rotary drive element having a drive surface adjacent said first drive shoe, said rotary drive element being rotatable from a first position to a second position responsive to contact of said drive surface by said first drive shoe; and
clamping structure for selectively clamping said rotary drive element to said rotor element.

12. The motor of claim 11, wherein said clamping structure includes a first field actuator clamping means adapted to vary in at least one dimension responsive to application or removal of an energy field.

13. The motor of claim 12, wherein said rotary drive element is disposed about said rotor element, and said first field actuator clamping means is carried by said rotary drive element and oriented to release said rotary drive element from said rotor element responsive to application of a said energy field to permit mutual rotation therebetween.

14. The motor of claim 11, further including means for returning said rotary drive element from said second position to said first position in the absence of said dimensional variance of said first field actuator drive means.

15. The motor of claim 14, wherein said rotary drive element return means comprises biasing means.

16. A motor comprising:
a stator member carrying a first and a second field actuator drive means, each of said drive means adapted to vary in at least one dimension responsive to the application or removal of an energy field;
an energy source for providing a said energy field;
a rotor element movable with respect to said stator member;
a first drive shoe in contact with said first and said second field actuator drive means, adjacent said rotor element and movable responsive to said dimensional variances of said first and said second field actuator drive means into and out of contact with said rotor element to effect movement thereof relative to said stator member; and
biasing means for maintaining said first drive shoe in contact with at least one of said first and second field actuator drive means during said dimensional variances thereof.

17. The motor of claim 16, wherein said first drive shoe is substantially rectangular, one of said field actuator drive means is in contact with a side thereof opposite a side adjacent said rotor element and the other of said field actuator drive means is in contact with a side of said first drive shoe perpendicular to the side contacted by said one field actuator drive means.

18. The motor of claim 16, wherein said rotor element includes an arcuate surface thereon adjacent said first drive shoe and an adjacent drive shoe side is curved to substantially the same radius as said rotor surface.

19. The motor of claim 16, wherein said first and second field actuator drive means, said biasing means and said drive shoe comprise a drive assembly for moving said rotor element, and said motor includes a plurality of said drive assemblies.

20. The motor of claim 19, wherein at least one of said plurality of drive assemblies is periodically subjected to a said energy field during periods which do not entirely coincide with periods over which at least another of said plurality of drive assemblies is subjected to a said energy field.

21. The motor of claim 16, wherein said first drive shoe is substantially rectangular, one of said field actuator drive means is in contact with a side thereof substantially perpendicular to said rotor element and the other of said field actuator drive means is in contact with said rotor element through a wedge means.

22. The motor of claim 21, wherein said first and second field actuator drive means are oriented substantially parallel to said rotor element and on opposite sides thereof.

23. A motor, comprising:
a stator member carrying a first field actuator drive means adapted to vary in at least one dimension responsive to application or removal of an energy field;

a rotor element movable with respect to said stator member;

a first linear reciprocable drive element in contact with said first field actuator drive means and linearly movable responsive to said dimensional variance of said first field actuator drive means;

a first clamping structure for selectively clamping said rotor element to said first reciprocable drive element; and an energy source for periodically subjecting said first field actuator drive means to a said energy field.

24. The motor of claim 23, further including a linear guide means for said rotor element oriented substantially parallel to said first linear drive element.

25. The motor of claim 23, further including second field actuator drive means adapted to vary in at least one dimension responsive to application or removal of an energy field, and a second linear reciprocable drive element in contact therewith and oriented substantially parallel to said first linear reciprocable drive element for linear movement responsive to said dimensional variance of said second field actuator drive means, and a second clamping structure for selectively clamping said rotor element to said second reciprocable drive element.

26. The motor of claim 16, wherein said first drive shoe is substantially triangular, each of said field actuator drive means is in contact with one of the sides of said triangle, and the third side of said triangle is adjacent said rotor element.

27. A motor, comprising:

a stator member carrying a first field actuator drive means adapted to vary in at least one dimension responsive to application or removal of an energy field;

an energy source for providing a said energy field;

a rotor element movable with respect to said stator member;

a first drive shoe in contact with said first field actuator drive means and movable responsive to said dimensional variance of said first field actuator to effect movement thereof relative to said stator member; and a first field actuator clamping means and a first clamping shoe in contact therewith and with said first drive shoe, said first field actuator clamping means being adapted to vary in at least one dimension responsive to application or removal of an energy field to move said first drive shoe into contact with said rotor element through said first clamping shoe.

28. The motor of claim 27, further including:

a second field actuator drive means carried by said stator and adapted to vary in at least one dimension responsive to application or removal of an energy field;

a second drive shoe in contact with said second field actuator drive means and movable responsive to said dimensional variance of said second field actuator to effect movement thereof relative to said stator member;

a second field actuator clamping means and a second clamping shoe in contact therewith and with said second drive shoe, said second field actuator clamping means being adapted to vary in at least one dimension responsive to application or removal of an energy field to move said second drive shoe into contact with said rotor element through said second clamping shoe.

29. The motor of claim 11, further including a second rotary drive element associated with said rotor element and having a drive surface adjacent a second drive shoe in contact with a second field actuator drive means adapted to vary in at least one dimension responsive to application or removal of an energy field, and a second clamping structure for selectively clamping said second rotary drive element to said rotor element.

30. The motor of claim 29, wherein said rotary drive elements are disposed about said rotor element, and said clamping structures are carded by their respective rotary drive elements.

31. The motor of claim 23, wherein said first linear reciprocable drive dement is in substantially coaxial contact with said first field actuator drive means.

* * * * *

UNITED STATES PATENT AND TRADEMARK OFFICE
CERTIFICATE OF CORRECTION

PATENT NO. : 5,432,395

DATED : 7/11/95

INVENTOR(S) : Allen R. Grahn

It is certified that error appears in the above-indentified patent and that said Letters Patent is hereby corrected as shown below:

Title page,
In the Abstract, line 1, insert a hyphen between "low" and "speed";

In Column 13, line 35, change "rotor" to --rotator--;

In Column 16, line 45, insert a comma after "300";

In Column 19, line 43, after "depicts" delete "a";

In Column 26, line 39, change "carded" to --carried--;

In Column 26, line 42, change "dement" to --element--.

Signed and Sealed this

Twenty-fourth Day of October, 1995

*Attest:*

BRUCE LEHMAN

*Attesting Officer*   Commissioner of Patents and Trademarks